United States Patent [19]

Sumimoto et al.

[11] Patent Number: 4,888,044
[45] Date of Patent: Dec. 19, 1989

[54] 3-PERFLUOROALKYL-5-SUBSTITUTED-OXY-ISOXAZOLE DERIVATIVES, PROCESS FOR PREPARING THE SAME, AND HERBICIDES CONTAINING THE SAME

[75] Inventors: Shinzaburo Sumimoto, Ashiya; Ichiro Ishizuka, Toyono; Shiro Ueda, Osaka; Hiroyuki Kai, Koka; Kinya Ide, Kusatsu, all of Japan

[73] Assignee: Shionogi & Co., Ltd., Osaka, Japan

[21] Appl. No.: 88,214

[22] Filed: Aug. 24, 1987

[30] Foreign Application Priority Data

Aug. 25, 1986 [JP] Japan .................. 61-199578

[51] Int. Cl.$^4$ .............. A01N 43/74; A01N 43/84; C07D 261/12; C07D 413/12
[52] U.S. Cl. ................. 71/88; 548/243; 548/247; 546/209; 544/137; 71/94
[58] Field of Search ........... 71/88, 94; 548/243; 544/137; 546/209

[56] References Cited

U.S. PATENT DOCUMENTS

| | | | |
|---|---|---|---|
| 4,540,430 | 9/1985 | Förster et al. | 71/90 |
| 4,645,525 | 2/1987 | Förster et al. | 548/243 |
| 4,756,741 | 7/1988 | Förster et al. | 71/88 |
| 4,788,291 | 11/1988 | Förster et al. | 71/90 |

FOREIGN PATENT DOCUMENTS 0018497 11/1980 European Pat. Off. .

Primary Examiner—Mukund J. Shah
Assistant Examiner—E. Bernhardt
Attorney, Agent, or Firm—Wenderoth, Lind & Ponack

[57] ABSTRACT

A novel herbicidal compound of the formula:

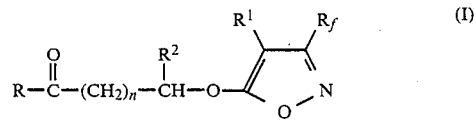

in which R is OH, $C_1$–$C_3$ alkoxy or $R^3$–N–$R^4$; $R_f$ is $C_1$–$C_3$ perfluoroalkyl; $R^1$ is hydrogen, $C_1$–$C_6$ alkyl or optionally substituted phenyl; $R^2$ is hydrogen or $C_1$–$C_3$ alkyl; n is an integer of 0 to 2; $R^3$ is hydrogen or $C_1$–$C_3$ alkyl; $R^4$ is $C_1$–$C_6$ alkyl, optionally substituted phenylalkyl where alkyl contains 1 to 3 carbons or optionally substituted phenyl; or $R^3$ and $R^4$ together with the nitrogen atom to which they are attached form a cyclic amino group; or a salt thereof. A process for preparing the compound (I) and a herbicide containing the compound (I) are also disclosed.

3 Claims, No Drawings

3-PERFLUOROALKYL-5-SUBSTITUTED-OXY-ISOXAZOLE DERIVATIVES, PROCESS FOR PREPARING THE SAME, AND HERBICIDES CONTAINING THE SAME

FIELD OF THE INVENTION

This invention relates to novel 3-perfluoroalkyl-5-substituted-oxy-isoxazoles, a process for producing them, and their use as herbicides.

BACKGROUND OF THE INVENTION

Some azole derivatives have been provided as herbicides. For example, Japanese Patent Laid Open Publication No. 147267/1980 discloses azolyloxy-carboxylic acid amides of the formula:

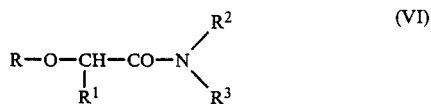

and their use as herbicides. EP-A-18497 discloses compounds having substituted acetic acid anilide structure of the formula:

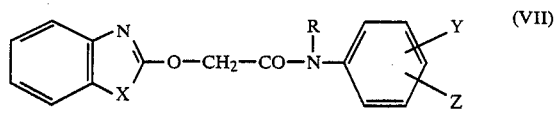

and their use as herbicides. EP-A-94541 discloses substituted 5-trifluoromethyl-1,3,4-thiadiazole-2-yl-oxyacetic acid amides of the formula:

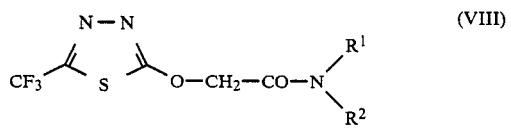

and their use as herbicides. However, no literature has disclosed 3-perfluoroalkyl-5-substituted-oxy-isoaozle derivatives.

It has been found that the 3-perfluoroalkyl-5-substituted-oxy-isoxaozle derivatives show a high selectivity, specifically on pre-emergence application, and herbicidal activity without producing any material phytotoxicity on various agricultural crops such as rice, wheat, soybean, cotton and the like.

SUMMARY OF THE INVENTION

The present invention provides compounds of the formula:

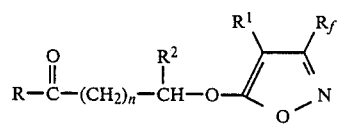

in which R is OH, $C_1$–$C_3$ alkoxy or $R^3$-N-$R^4$; $R_f$ is $C_1$–$C_3$ perfluoroalkyl; $R^1$ is hydrogen, $C_1$–$C_6$ alkyl or optionally substituted phenyl; $R^2$ is hydrogen or $C_1$–$C_3$ alkyl; n is an integer of 0 to 2; $R^3$ is hydrogen or $C_1$–$C_3$ alkyl; $R^4$ is $C_1$–$C_6$ alkyl, optionally substituted phenylalkyl where alkyl contains 1 to 3 carbons or optionally substituted phenyl; or $R^3$ and $R^4$ together with the nitrogen atom to which they are attached from a cyclic amino group; or a salt thereof, a process for producing them and their use as herbicides.

DISCLOSURE OF THE INVENTION

In the above formula (I), example of $C_1$–$C_3$ alkoxy for R includes methoxy, ethoxy, isopropoxy etc. Example of $C_1$–$C_3$ perfluoroalkyl for $R_f$ includes trifluoromethyl, pentafluoroethyl, heptafluoropropyl etc. Example of $C_1$–$C_6$ alkyl for $R^1$ includes methyl, ethyl, propyl, cyclohexyl etc. Example of optionally substituted phenyl includes phenyl, 4-fluorophenyl, 4-chlorophenyl, 4-methylphenyl, 4-methoxyphenyl, 3,4-dimethoxyphenyl, 3,4methylenedioxyphenyl etc. Example of $C_1$–$C_3$ alkyl for $R^2$ includes methyl, ethyl, isopropyl etc. Example of $C_1$–$C_6$ alkyl for $R^3$ or $R^4$ includes methyl, ethyl, propyl, isopropyl, isobutyl, hexyl, cyclohexyl etc. Example of optionally substituted phenylalkyl, where alkyl contains includes $C_1$–$C_3$ carbons, includes benzyl, α-methylbenzyl, α,α-dimethylbenzyl, phenylethyl, phenylpropyl etc. Example of optionally substituted phenyl includes phenyl, 2-methylphenyl, 3-methylphenyl, 4-ethyl-ethylphenyl, 2-chlorophenyl, 3-chlorophenyl, 4-chlorophenyl, 2-methoxyphenyl, 4-methoxyphenyl, 3-trifluoromethylphenyl, 3,5-dichlorophenyl, 3-methylthiophenyl, 3-nitrophenyl etc. Example of a cyclic amino group for $R^3$ and $R^4$, formed together with nitrogen atom to which they are attached, includes 2-methylpiperidino, 2-ethylpiperidino, morpholino, pyrrolidino etc.

3-Perfluoroalkyl-5-substituted-oxy-isoxazole derivatives of the present invention can be prepared by the following procedure.

(a) It can be prepared by the reaction of a compound of formula:

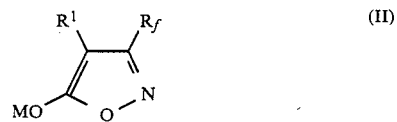

in which $R_f$ and $R^1$ are as defined above and M is hydrogen or alkali metal atom, with a compound of the formula:

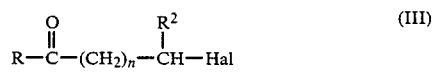

in which R, $R^2$, $R^3$, $R^4$ and n are as defined above and Hal is halogen, in the presence of a basic substance in an inert solvent as necessary, at 0°–150° C., preferably at 30°–100° C., for 2–200 hours, preferably for 8–100 hours and the treatment of the resulting product by conventional techniques.

Example of the inert solvent includes acetonitrile, toluene, dioxane, tetrahydrofuran, dimethylformamide, dimethylsulfoxide, acetone, methyl ethyl ketone etc.

Example of alkali metal atom for M includes sodium, potassium, lithium etc.

Example of halogen for Hal includes chlorine, bromine etc.

(b) It can be prepared by the reaction of a compound of the formula:

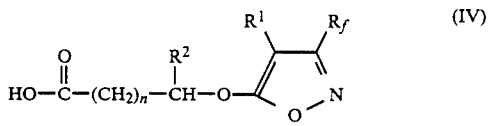

in which $R_f$, $R^1$, $R^2$ and n are as defined above, with a compound of the formula:

in which $R^3$ and $R^4$ are as defined above, in the presence of a condensing agent in an inert solvent as necessary, at 0°–100° C., preferably at 20°–70° C., for 0.1–50 hours, preferably for 0.5–20 hours and the treatment of the resulting product by conventional techniques.

Example of the inert solvent includes tetrahydrofuran, dioxane etc. Example of the condensing agent includes DCC, polyphosphoric acid etc.

(c) It can be prepared by the reaction of a compound of the formula:

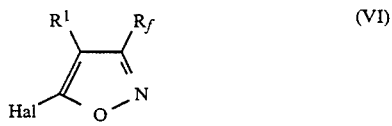

in which $R_f$, $R^1$ and Hal are as defined above, with a compound of the formula:

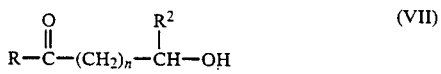

in which R, $R^2$, $R^3$, $R^4$ and n are as defined above, in the presence of a basic substance in an inert solvent as necessary, at 0°–100° C., preferably at 20°–80° C. for 2–50 hours, preferably for 8–24 hours and the treatment of the resulting product by conventional techniques.

Example of an inert solvent includes tetrahydrofuran, dioxane, toluene etc. Example of a basic substance includes potassium t-butoxide, sodium hydrate etc. Example of halogen for Hal includes chlorine, bromine etc.

The compounds of the formula (III) and (V)–(VII) used as the starting material is known or can be made by known method.

The compound of the formula (II) can be prepared by the method described in EP-A-220025. The preparation method of the compound of the formula (IV) has been described in Preparation 3.

When the compound (I) of the present invention is used as the active ingredient of a herbicide, the dosage rate may vary on the purpose of use, weed species, the dosage rate is from 0.1 to 50 g, preferably from 1 to 30 g, of the active ingredient per are and the formulation may be applied as such without dilution or with dilution.

On the practical usage of the presently invented compound (I) as a herbicide, it may be applied in any preparation form such as dust, granules, an emulsion, wettable powder, a suspension and the like in combination with, as necessary, a conventional solid or liquid carrier, a combination carrier of conventional solid and liquid carriers, a surface active agent and/or an auxiliary agents.

The content of the present compound (I) as the active ingredient in said preparation form may be usually within a range of 1 to 80% by weight, preferably of 1 to 50% by weight.

As the solid carrier or diluent, there may be used clay (e.g. kaolin clay, attapulgite clay) bentonite, terra alba, pyrophyllite, talc, diatomaceous earth, silica, calcite, wallnut-shell powder, urea, ammonium sulfate, synthetic hydrated silica, etc. Example of the liquid carrier or diluent are water, aromatic hydrocarbons (e.g. benzene, toluene, xylene, methylnaphthalene), alcohols (e.g. isopropanol, ethylene glycol, cellosolve), ketones (e.g. acetone, cyclohexanone, isophorone), vegetable oils (e.g. soybean oil, cotton-seed oil), dimethyl sulfoxide, acetonitrile, cyclohexane, etc.

Examples of the surface active agent are the anionic type such as alkylsulfates, alkylarylsulfonates, dialkylsulfosuccinates, phosphates of polyoxyethylenealkylaryl ethers, etc. and the non-ionic type such as polyoxyethylene alkyl ethers, polyoxyethylene alkylaryl ethers, polyoxyethylene polyoxypropylene black copolymers, sorbitan fatty acid esters, polyoxyethylene sorbitan fatty acid esters, etc. The surface active agents have the actions such as emulsification, dispersion and wetting.

According to the purpose of an application, there can be added suitable auxiliaries such as emulsifiers, stabilizers, dispersing agents, suspension, spreaders, penetrating agents, wetting agents and the like, for example, ligninsulfonates, alginates, polyvinylalcohol, gum arabic, CMC (carboxymethyl cellulose), PAP (isopropyl acid phosphate), polyoxyethylene resin acid esters, abietates, dinaphthylmethanedisulfonates etc.

In general, the presently invented compounds formulated in any suitable formulation form are used by soil or foliar treatment. When the formulation is used by soil treatment, it is spread over the soil surface (if necessary, incorporated it into the soil). Examples of the soil applied are sandy loam, usual soil such as loamy soil, clayey soil, sandy soil and the like. The present compounds may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

The following examples, preparations and formulation examples further illustrate the present invention in detail but are not to be construed to limit the scope thereof.

Example 1

N-Methyl-N-(3-methylphenyl)-2-(3-trifluoromethyl-5-isoxazolyloxy)acetamide

To 2.23 g (10 mmole) of 3-trifluoromethyl-5-hydroxy isoxazole sodium salt (purity 78.6%) were added dry acetonitrile (35 ml) and N-methyl-N-(3-methylphenyl)-2-bromoacetamide (3.15 g) and the resulting mixture was stirred at 60° C. for 24 hours. The reaction solution was evaporated under reduced pressure and the residue was mixed with water (35 ml), extracted with methylene chloride, treated with anhydrous sodium sulfate and concentrated under reduced pressure. The residue was purified by chromatography on silica gel to give 2.09 g of crystals. After these were dissolved in benzene, n-hexane was added gradually and the precipitated crystals were filtered off to give 1.96 g of the tilted compound as colorless prisms, yield 62.4%, m.p. 54.0°–55.5° C.

Anal. Calcd. for $C_{14}H_{13}N_2O_3F_3$: C, 53.51; H, 4.17; N, 8.91. Found C, 53.52; H, 4.11; N, 8.82.

Example 2

N-Ethyl-N-phenyl-2-(3-trifluoromethyl-5-isoxazolyloxy)acetamide (i) To 1.80 g (8.0 mmole) of methyl 2-(3-trifluoromethyl-5-isoxazolyloxy)acetate was added a 1% solution of NaOH (38.40 g, 9.6 mmole) and the resulting mixture was stirred at room temperature for one hour. After being adjusted to pH 1 with conc. HCl with ice cooling, the solution was extracted with diethyl ether. The ether layer was dried with anhydrous sodium sulfate and diethyl ether was evaporated under reduced pressure to give 1.68 g of colorless crystals. These were recrystallized from benzenecyclohexane to give 1.60 g of 2-(3-trifluoromethyl-5-ixoxazolyloxy)acetic acid as colorless plates, yield 94.7%, m.p. 99.0°–100° C.

Anal. Calcd. for $C_6H_4NO_4F_3$: C, 34.14; H, 1.19; N, 6.64. Found: C, 33.85; H, 2.13; N, 7.13.

(ii) 1.30 ml (2.37 mmole) of N-ethylaniline and 0.50 g (2.37 mmole) of 2-(3-trifluoromethyl-5-isoxazolyloxy)acetic acid were dissolved in 2.4 ml of dry THF and to the solution was added 0.60 g (2.61 mmole) of dicyclohexylcarbodiimide. After being stirred at room temperature for one hour, the reaction mixture was allowed to stand overnight at room temperature. After the addition of glacial acetic acid (0.2 ml), the mixture was stirred at room temperature for 30 minutes and the precipitated crystals were filtered off. The filtrate was evaporated under reduced pressure and the residue was purified by chromatography on silica gel to give 638 mg of the titled compound as a pale red viscous liquid, yield 85.7%.

IR(CHCl₃; cm⁻¹): 1680, 1610, 1494.

Anal. Calcd. for $C_{14}H_{13}N_2O_3F_3$: C, 53.51; H, 4.17; N, 8.91. Found: C, 54.06; H, 4.32; N, 9.15

Example 3

N-Methyl-N-phenyl-2-(3-trifluoromethyl-4-phenyl-5-isoxazolyloxy)acetamide 0.99 g (6.0 mmole) of N-methyl-N-phenyl-2-hydroxyacetamide was dissolved in THF (6 ml) and the solution was mixed with 0.75 g (6.0 mmole) of 90% potassium t-butoxide with ice cooling. The mixture was stirred for 30 minutes and then 1.24 g (5.0 mmole) of 3-trifluoromethyl-4-phenyl-5-chloroisoxazole was added dropwise to the mixture. After being stirred for 30 minutes, the mixture was refluxed for 24 hours. After cooling the reaction mixture, 60 ml of methylene chloride was added and the mixture was washed with a 5% solution of HCl and water. The methylene chloride phase was evaporated under reduced pressure and the residue was purified by chromatography on silica gel to give 1.15 g of colorless crystals. These were recrystallized from n-hexane to give 950 mg of the titled compound, yield 50.5%, m.p. 93.0°–94.0° C.

Anal. Calcd. for $C_9H_{15}N_2O_3F_3$: C, 60.63; H, 4.03; N, 7.44; F, 15.15. Found: C, 61.01; H, 4.35; N, 7.39; F, 15.22.

Example 4

Methyl 2-(3-trifluoromethyl-4-methyl-5-isoxazolyloxy)acetate

To 1.00 g (6 mmole) of 3-trifluoromethyl-4-methyl-5-hydroxyisoxazole were added 10 ml of dry acetone and 1.00 g (7.2 mmole) of anhydrous potassium carbonate and the resulting mixture was stirred at room temperature for one hour. After addition of methyl bromoacetate (1.10 g, 7.2 mmole), the mixture was refluxed for 30 hours. The reaction mixture was mixed with water (100 ml) and, extracted with diethyl ether. The diethyl ether phase was dried with anhydrous magnesium sulfate, evaporated under reduced pressure, and the residue was purified by chromatography on silica gel to give 0.73 g of the title compound as colorless viscous liquid, yield 53.6%.

Example 5

N-Methyl-N-phenyl-2-(3-pentafluoroethyl-5-isoxazolyloxy)acetamide

To 0.50 g (2.2 mmole) of 3-pentafluoroethyl-5-hydroxyisoxazole sodium salt were added dry acetonitrile (7 ml) and N-methyl-N-phenyl-2-bromoacetamide (0.55 g) and the resulting mixture was stirred at 60° C. for 24 hours. After completion of reaction, the reaction solution was evaporated under reduced pressure and to the residue was added water (80 ml), extracted with methylene chloride, treated with anhydrous sodium sulfate and concentrated under reduced pressure. The residue was purified by chromatography on silica gel to give 0.52 g of crystals. These crystals were recrystallized from n-hexane to give 0.48 g of the titled compound as colorless plates, yield 62.3%, m.p. 88.0–89.0° C.

Anal. Calcd. for $C_{14}H_{11}N_2O_3F_5$: C, 48.00; H, 3.17; N, 8.00. Found: C, 47.83; H, 3.32; N, 8.05.

Examples 6 to 128

The following compounds were prepared according to the same procedure as described in examples 1 to 5. The results are shown in Tables 1 and 2.

In the tables, boiling points (b.p.) were shown in °C./mmHg, melting points (m.p.) were shown in °C. and infrared spectra were measured in CHCl₃ and shown in cm⁻¹.

TABLE 1

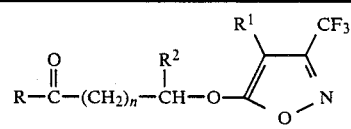

| Ex. No. | R | n | R² | R¹ | Yield (%) | Physical property | Appearance |
|---|---|---|---|---|---|---|---|
| 6 | CH₃O | 0 | H | H | 31.7 | b.p: 75–76/0.50 | colorless liquid |
| 7 | HO | 0 | CH₃ | H | 89.4 | mp: | colorless |

TABLE 1-continued $$R-\overset{O}{\underset{\|}{C}}-(CH_2)_n-\overset{R^2}{\underset{|}{CH}}-O-\underset{\underset{O}{\diagdown}\diagup}{\overset{R^1\diagup\diagdown CF_3}{\diagdown\diagup}}N$$

| Ex. No. | R | n | R² | R¹ | Yield (%) | Physical property | Appearance |
|---|---|---|---|---|---|---|---|
| 8 | CH₃O | 0 | CH₃ | H | 79.4 | 56.0–58.0 IR: 1756, 1160, 1100 | needles colorless liquid |
| 9 | CH₃O | 0 | CH₃ | CH₃ | 74.2 | IR: 1750, 1480, 1150 | pale yellow liquid |
| 10 | CH₃O | 0 | CH₃ | phenyl | 84.1 | IR: 1756, 1480, 1150 | colorless liquid |
| 11 | CH₃O | 0 | CH₃ | 4-Cl-C₆H₄ | 64.9 | IR: 1750, 1485, 1150 | pale yellow liquid |
| 12 | CH₃O | 0 | CH₃ | 4-CH₃O-C₆H₄ | 78.6 | IR: 1755, 1485, 1180 | colorless liquid |
| 13 | (CH₃)₂N— | 0 | H | H | 46.2 | IR: 1678, 1160, 1100 | pale yellow liquid |
| 14 | (C₂H₅)₂N— | 0 | H | H | 41.0 | IR: 1665, 1160, 1100 | pale yellow liquid |
| 15 | CH₃(C₆H₁₃)N— | 0 | H | H | 54.7 | IR: 1660, 1614, 1158 | thin brown viscous liquid |
| 16 | CH₃(cyclohexyl)N— | 0 | H | H | 39.6 | IR: 1666, 1612, 1100 | thin brown viscous liquid |
| 17 | CH₃(PhCH₂)N— | 0 | H | H | 17.5 | IR: 1676, 1614, 1496 | thin yellow green viscous liquid |
| 18 | CH₃(Ph(CH₃)CH)N— | 0 | H | H | 44.2 | IR: 1663, 1612, 1096 | thin yellow green viscous liquid |
| 19 | 2-methylpiperidin-1-yl | 0 | H | H | 61.6 | IR: 1660, 1160, 1105 | thin yellow green viscous liquid |

TABLE 1-continued $$R-\underset{\underset{O}{\|}}{C}-(CH_2)_n-\underset{\underset{R^2}{|}}{CH}-O-\underset{\underset{O-N}{}}{\overset{R^1\quad CF_3}{\diagup}}$$

| Ex. No. | R | n | R² | R¹ | Yield (%) | Physical property | Appearance |
|---|---|---|---|---|---|---|---|
| 20 | 2-ethylpiperidinyl | 0 | H | H | 65.3 | mp: 50.0–52.0 | pale yellow prisms |
| 21 | 2-methylpiperidinyl | 0 | H | phenyl | 71.9 | mp: 123.0–124.0 | colorless prisms |
| 22 | 2-ethylpiperidinyl | 0 | H | phenyl | 69.4 | IR: 1660, 1490, 1152 | colorless viscous liquid |
| 23 | HO | 0 | H | CH₃ | 84.9 | mp: 77.0–78.0 | colorless plates |
| 24 | HO | 0 | H | phenyl | 70.4 | mp: 112.0–114.0 | colorless prisms |
| 25 | (CH₃)₂N– | 0 | H | phenyl | 65.8 | mp: 114.0–115.0 | colorless prisms |
| 26 | CH₂=CHCH₂, H₅C₂OCH₂C(O)– N– | 0 | H | CH₃ | 72.3 | IR: 1680, 1490, 1150 | pale yellow viscous liquid |
| 27 | 2-ethylpiperidinyl | 0 | H | CH₃ | 98.4 | IR: 1660, 1490, 1060 | pale brown viscous liquid |

TABLE 2

$$\underset{R^4}{\overset{R^3}{\diagdown}}N-\underset{\underset{O}{\|}}{C}-(CH_2)_n-\underset{\underset{R^2}{|}}{CH}-O-\underset{\underset{O-N}{}}{\overset{R^1\quad CF_3}{\diagup}}$$

| Ex. No. | R⁴ | R³ | n | R² | R¹ | Yield (%) | Physical property | Appearance |
|---|---|---|---|---|---|---|---|---|
| 28 | phenyl | CH₃ | 0 | H | H | 39.1 | mp: 67.0–68.0 | colorless plates |
| 29 | phenyl | CH₃ | 0 | H | C₂H₅ | 77.3 | mp: 56.0–59.0 | colorless crystals |

TABLE 2-continued

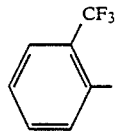

| Ex. No. | R⁴ | R³ | n | R² | R¹ | Yield (%) | Physical property | Appearance |
|---|---|---|---|---|---|---|---|---|
| 30 | 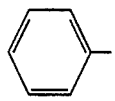 | CH₃ | 0 | H | H | 60.8 | mp: 52.5–53.5 | colorless powder |
| 31 | 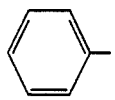 | CH₃ | 0 | CH₃ | H | 56.5 | IR: 1666, 1608, 1490 | colorless viscous liquid |
| 32 | 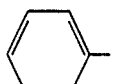 | CH₃ | 0 | H | CH₃ | 63.6 | mp: 58.0–60.0 | colorless crystals |
| 33 | 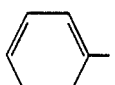 | CH₃ | 0 | CH₃ | CH₃ | 80.4 | IR: 1676, 1488, 1156 | colorless liquid |
| 34 | 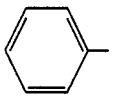 | CH₃ | 1 | H | 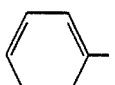 | 23.3 | IR: 1640, 1494, 1152 | thin yellow viscous liquid |
| 35 | 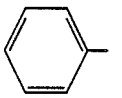 | CH₃ | 0 | CH₃ | 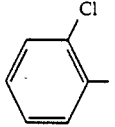 | 87.1 | IR: 1674, 1490, 1154 | colorless viscous liquid |
| 36 | 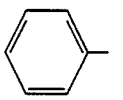 | CH₃ | 0 | H | 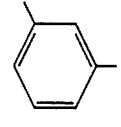 | 65.7 | mp: 90.0–91.0 | colorless prisms |
| 37 | 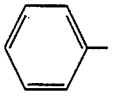 | CH₃ | 0 | H | 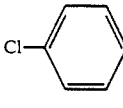 | 49.9 | mp: 85.5–86.5 | colorless prisms |
| 38 | 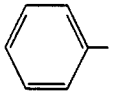 | CH₃ | 0 | H | 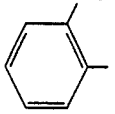 | 69.0 | mp: 84.0–84.5 | colorless plates (efforescence) |
| 39 | 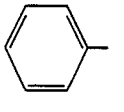 | CH₃ | 0 | H | 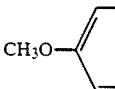 | 50.5 | mp: 92.5–93.0 | colorless prisms |
| 40 | 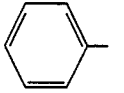 | CH₃ | 0 | H | | 64.5 | mp: 53.0–54.5 | colorless solid |

TABLE 2-continued

| Ex. No. | R⁴ | R³ | n | R² | R¹ | Yield (%) | Physical property | Appearance |
|---|---|---|---|---|---|---|---|---|
| 41 | CH₃S—C₆H₄— | CH₃ | 0 | H | C₆H₅— | 87.9 | mp: 88.0–90.0 | colorless crystals |
| 42 | CH₃—C₆H₄— | CH₃ | 0 | H | C₆H₅— | 75.1 | mp: 79.0–79.5 | colorless prisms |
| 43 | C₂H₅—C₆H₄— | CH₃ | 0 | H | C₆H₅— | 70.6 | mp: 59.0–62.0 | colorless solid |
| 44 | CF₃—C₆H₄— | CH₃ | 0 | H | C₆H₅— | 69.2 | mp: 115.5–116.0 | colorless needles |
| 45 | Cl,Cl—C₆H₃— | CH₃ | 0 | H | C₆H₅— | 32.7 | mp: 114.0–115.0 | colorless needles |
| 46 | Cl,Cl—C₆H₃— | (CH₃)₂CH— | 0 | H | C₆H₅— | 66.7 | mp: 155.0–156.0 | colorless needles |
| 47 | C₆H₅— | CH₃ | 0 | H | F—C₆H₄— | 56.7 | mp: 100.0–101.5 | colorless prisms |
| 48 | C₆H₅— | CH₃ | 0 | H | Cl—C₆H₄— | 48.7 | mp: 101.0–102.0 | colorless needles |
| 49 | C₆H₅— | CH₃ | 0 | CH₃ | Cl—C₆H₄— | 45.5 | mp: 90.5–92.0 | colorless prisms |
| 50 | CH₃—C₆H₄— | CH₃ | 0 | H | Cl—C₆H₄— | 71.1 | mp: 94.5–96.0 | colorless needles |

TABLE 2-continued

| Ex. No. | R⁴ | R³ | n | R² | R¹ | Yield (%) | Physical property | Appearance |
|---|---|---|---|---|---|---|---|---|
| 51 | 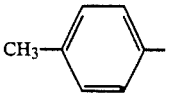 | CH₃ | 0 | H | 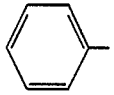 (CH₃-) | 62.8 | mp: 97.0–98.0 | colorless prisms |
| 52 | 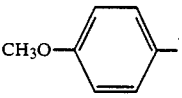 | CH₃ | 0 | H | 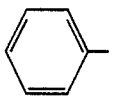 (CH₃O-) | 72.2 | mp: 133.0–134.0 | colorless prisms |
| 53 | 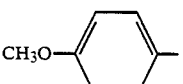 | CH₃ | 0 | CH₃ | 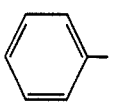 (CH₃O-) | 74.5 | mp: 81.0–82.0 | colorless prisms |
| 54 | 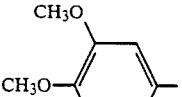 | CH₃ | 0 | H | 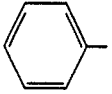 (CH₃O, CH₃O-) | 27.5 | mp: 104.0–105.0 | colorless prisms |
| 55 |  | CH₃ | 0 | H | 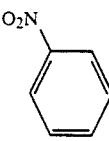 (methylenedioxyphenyl) | 74.6 | mp: 99.5–100.5 | colorless prisms |
| 56 | 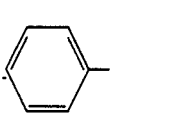 (O₂N-) | CH₃ | 0 | H | 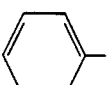 | 67.8 | mp: 128.0–130.0 | pale yellow crystals |
| 57 | 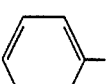 | C₂H₅ | 0 | H | CH₃ | 93.4 | mp: 75.0–77.0 | colorless prisms |
| 58 | 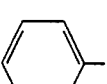 | n-C₃H₇ | 0 | H | CH₃ | 97.8 | mp: <30.0 IR: 1670, 1480, 1140 | pale yellow crystals |
| 59 | 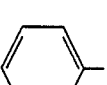 | —CH(CH₃)₂ | 0 | H | CH₃ | 90.3 | mp: 49.0–50.0 | colorless crystals |
| 60 | 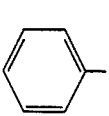 | n-C₄H₉ | 0 | H | CH₃ | 93.5 | IR: 1675, 1490, 1150 | colorless viscous liquid |
| 61 | 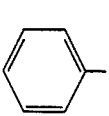 | n-C₅H₁₁ | 0 | H | CH₃ | 95.4 | IR: 1670, 1480, 1140 | pale yellow viscous liquid |

TABLE 2-continued

Structure:
$R_3R_4N-C(=O)-(CH_2)_n-CH(R^2)-O-$[isoxazole with $R^1$ at 4-position and $CF_3$ at 3-position]

| Ex. No. | R⁴ | R³ | n | R² | R¹ | Yield (%) | Physical property | Appearance |
|---|---|---|---|---|---|---|---|---|
| 62 | 2-CH₃-C₆H₄ | CH₃ | 0 | H | CH₃ | 86.4 | mp: 81.0–82.0 | colorless granular crystals |
| 63 | 2-C₂H₅-C₆H₄ | CH₃ | 0 | H | CH₃ | 77.9 | mp: 86.0–88.0 | colorless crystals |
| 64 | 2-i-Pr-C₆H₄ | CH₃ | 0 | H | CH₃ | 79.9 | mp: 74.0–76.0 | colorless crystals |
| 65 | 2-Ph-C₆H₄ | CH₃ | 0 | H | CH₃ | 90.6 | mp: 82.0–84.0 | colorless crystals |
| 66 | 2-OCH₃-C₆H₄ | CH₃ | 0 | H | CH₃ | 87.1 | IR: 1675, 1488, 1060 | colorless viscous liquid |
| 67 | 2-F-C₆H₄ | CH₃ | 0 | H | CH₃ | 96.3 | IR: 1680, 1145, 1060 | colorless viscous liquid |
| 68 | 2-Cl-C₆H₄ | CH₃ | 0 | H | CH₃ | 53.2 | mp: 73.0–75.0 | colorless crystals |
| 69 | 2-I-C₆H₄ | CH₃ | 0 | H | CH₃ | 75.1 | mp: 92.0–94.0 | colorless crystals |
| 70 | 3-CH₃-C₆H₄ | CH₃ | 0 | H | CH₃ | 89.9 | mp: 36.0–39.0 | colorless crystals |
| 71 | 3-C₂H₅-C₆H₄ | CH₃ | 0 | H | CH₃ | 77.9 | IR: 1670, 1485, 1145 | colorless viscous liquid |

TABLE 2-continued $$\underset{R_4}{\overset{R_3}{N}}-\underset{\|}{\overset{O}{C}}-(CH_2)_n-\underset{R^2}{\overset{R^2}{CH}}-O-\underset{\underset{N}{\overset{O}{\diagdown}}}{\overset{R^1}{\diagup}}\overset{CF_3}{\diagdown}$$

| Ex. No. | R⁴ | R³ | n | R² | R¹ | Yield (%) | Physical property | Appearance |
|---|---|---|---|---|---|---|---|---|
| 72 | CH₃O—C₆H₄— (m) | CH₃ | 0 | H | CH₃ | 96.8 | IR: 1675, 1483, 1145 | colorless viscous liquid |
| 73 | CH₃S—C₆H₄— (m) | CH₃ | 0 | H | CH₃ | 83.2 | mp: 66.0–67.0 | colorless crystals |
| 74 | CH₃OC—C₆H₄— (m) | CH₃ | 0 | H | CH₃ | 95.4 | mp: 44.0–46.0 | pale yellow crystals |
| 75 | CF₃—C₆H₄— (m) | CH₃ | 0 | H | CH₃ | 80.2 | mp: 84.0–85.0 | colorless crystals |
| 76 | F—C₆H₄— (m) | CH₃ | 0 | H | CH₃ | 88.3 | mp: 50.0–52.0 | pale yellow crystals |
| 77 | Cl—C₆H₄— (m) | CH₃ | 0 | H | CH₃ | 95.6 | mp: 65.0–67.0 | colorless crystals |
| 78 | O₂N—C₆H₄— (m) | CH₃ | 0 | H | CH₃ | 66.4 | mp: 94.0–95.0 | colorless needles |
| 79 | CH₃—C₆H₄— (p) | CH₃ | 0 | H | CH₃ | 89.3 | IR: 1675, 1490, 1150 | pale yellow viscous liquid |
| 80 | C₂H₅—C₆H₄— (p) | CH₃ | 0 | H | CH₃ | 91.5 | mp: 74.0–76.0 | pale yellow crystals |
| 81 | n-Bu—C₆H₄— (p) | CH₃ | 0 | H | CH₃ | 82.8 | IR: 1670, 1495, 1145 | colorless viscous liquid |

TABLE 2-continued $$\underset{R^4}{\overset{R_3}{N}}-\overset{O}{\underset{}{C}}-(CH_2)_n-\overset{R^2}{\underset{}{CH}}-O-\underset{O-N}{\overset{R^1\quad CF_3}{\text{isoxazole}}}$$

| Ex. No. | R⁴ | R³ | n | R² | R¹ | Yield (%) | Physical property | Appearance |
|---|---|---|---|---|---|---|---|---|
| 82 | 4-F-C₆H₄- | CH₃ | 0 | H | CH₃ | 86.2 | mp: 50.0–52.0 | colorless crystals |
| 83 | 4-Cl-C₆H₄- | CH₃ | 0 | H | CH₃ | 89.8 | mp: 99.0–101.0 | colorless crystals |
| 84 | 2,3-(CH₃)₂-C₆H₃- | CH₃ | 0 | H | CH₃ | 83.5 | mp: 93.0–95.0 | colorless crystals |
| 85 | 2,4-(CH₃)₂-C₆H₃- | CH₃ | 0 | H | CH₃ | 77.9 | mp: 66.0–68.0 | colorless crystals |
| 86 | 2,6-(CH₃)₂-C₆H₃- | CH₃ | 0 | H | CH₃ | 94.0 | mp: 113.0–114.5 | colorless crystals |
| 87 | 2,6-(C₂H₅)₂-C₆H₃- | CH₃ | 0 | H | CH₃ | 83.1 | mp: 74.0–76.0 | colorless crystals |
| 88 | 2,6-F₂-C₆H₃- | CH₃ | 0 | H | CH₃ | 79.9 | mp: 60.0–63.0 | colorless crystals |
| 89 | C₆H₅- | CH₃ | 0 | H | n-C₄H₉ | 45.6 | IR; 1675, 1480, 1145 | colorless viscous liquid |
| 90 | 3-CH₃-C₆H₄- | CH₃ | 0 | H | 4-F-C₆H₄- | 63.7 | mp: 77.0–79.0 | colorless crystals |

TABLE 2-continued

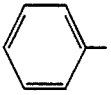

| Ex. No. | R⁴ | R³ | n | R² | R¹ | Yield (%) | Physical property | Appearance |
|---|---|---|---|---|---|---|---|---|
| 91 | 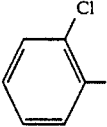 | C₂H₅ | 0 | H | H | 85.7 | IR: 1680, 1610, 1494 | red viscous liquid |
| 92 | 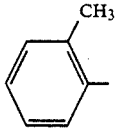 | CH₃ | 0 | H | C₂H₅ | 64.4 | mp: 59.0–61.0 | colorless crystals |
| 93 | 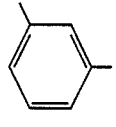 | CH₃ | 0 | H | C₂H₅ | 92.6 | mp: 51.0–54.0 | pale yellow crystals |
| 94 | 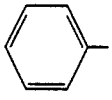 | CH₃ | 0 | H | C₂H₅ | 91.0 | mp: 40.0–46.0 | reddish brown crystals |
| 95 | 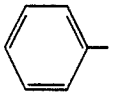 | C₂H₅ | 0 | H | 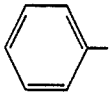 | 95.1 | mp: 97.0–99.0 | colorless crystals |
| 96 | 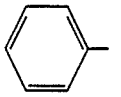 | n-C₃H₇ | 0 | H | 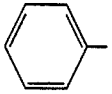 | 95.4 | mp: 75.0–77.0 | colorless crystals |
| 97 | 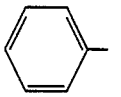 | —CH(CH₃)₂ | 0 | H | 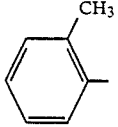 | 81.2 | mp: 85.0–87.0 | colorless crystals |
| 98 | 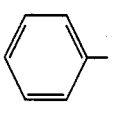 | CH₃ | 0 | H | 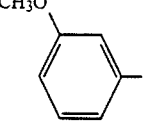 | 91.5 | mp: 88.0–90.0 | colorless crystals |
| 99 | 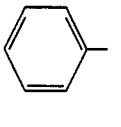 | CH₃ | 0 | H | 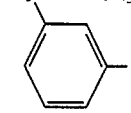 | 91.4 | mp: 82.9–84.0 | pale yellow crystals |
| 100 | 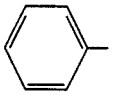 | CH₃ | 0 | H |  | 91.9 | mp: 95.0–98.0 | colorless crystals |

TABLE 2-continued $$\underset{R^4}{\overset{R_3}{\text{N}}}-\overset{\overset{\text{O}}{\|}}{\text{C}}-(\text{CH}_2)_n-\overset{R^2}{\underset{}{\text{CH}}}-\text{O}\diagdown\overset{R^1}{\underset{\text{N}}{\diagup}}\text{CF}_3$$

| Ex. No. | R⁴ | R³ | n | R² | R¹ | Yield (%) | Physical property | Appearance |
|---|---|---|---|---|---|---|---|---|
| 101 | 2,6-(CH₃)₂-C₆H₃ | CH₃ | 0 | H | Ph | 91.8 | mp: 114.0–115.0 | colorless crystals |
| 102 | 2-C₂H₅-C₆H₄ | CH₃ | 0 | H | Ph | 70.1 | mp: 69.0–70.0 | colorless crystals |
| 103 | 2-i-Pr-C₆H₄ | CH₃ | 0 | H | Ph | 71.7 | mp: 101.0–103.0 | colorless crystals |
| 104 | 2-Ph-C₆H₄ | CH₃ | 0 | H | Ph | 75.5 | mp: 121.0–123.0 | colorless crystals |
| 105 | 2-F-C₆H₄ | CH₃ | 0 | H | Ph | 76.1 | mp: 68.0–72.0 | colorless crystals |
| 106 | 2-I-C₆H₄ | CH₃ | 0 | H | Ph | 63.0 | mp: 85.0–86.0 | colorless crystals |
| 107 | 4-CH₃-C₆H₄ | CH₃ | 0 | H | Ph | 79.0 | mp: 41.0–43.0 | pale yellow crystals |
| 108 | 4-n-Bu-C₆H₄ | CH₃ | 0 | H | Ph | 80.9 | IR: 1675, 1485, 1150 | pale yellow viscous liquid |
| 109 | 3-H₃COC-C₆H₄ | CH₃ | 0 | H | Ph | 77.7 | mp: 76.5–79 | colorless crystals |

TABLE 2-continued
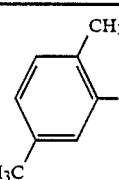
| Ex. No. | R⁴ | R³ | n | R² | R¹ | Yield (%) | Physical property | Appearance |
|---|---|---|---|---|---|---|---|---|
| 110 |  | CH₃ | 0 | H | 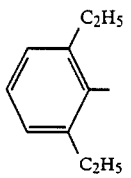 | 90.7 | mp: 76.0–78.0 | pale brown crystals |
| 111 |  | CH₃ | 0 | H | 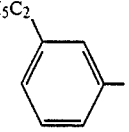 | 84.8 | mp: 53.0–55.0 | pale yellow crystals |
| 112 |  | CH₃ | 0 | H | 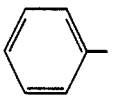 | 82.4 | mp: 75.0–77.0 | pale yellow crystals |
| 113 | 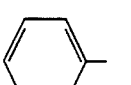 | H | 0 | CH₃ | CH₃ | 47.7 | mp: 82.0–84.0 | colorless plates |
| 114 | 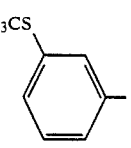 | H | 0 | H | CH₃ | 71.0 | mp: 88.0–89.0 | colorless needles |
| 115 | 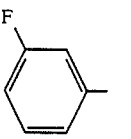 | H | 0 | H | CH₃ | 78.9 | mp: 84.0–85.0 | colorless plates |
| 116 |  | CH₃ | 0 | H | 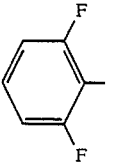 | 95.1 | mp: 71.0–73.0 | colorless prisms |
| 117 |  | CH₃ | 0 | H | 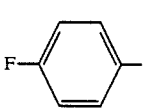 | 93.0 | mp: 68.0–70.0 | colorless crystals |
| 118 |  | CH₃ | 0 | H | | 84.5 | IR: 1680, 1490, 1155 | colorless viscous liquid |

TABLE 2-continued $$\underset{R^4}{\overset{R_3}{\text{N}}}-\overset{\overset{O}{\|}}{\text{C}}-(CH_2)_n-\overset{R^2}{\text{CH}}-O-\underset{\underset{N}{\overset{\text{O}}{\diagdown}}}{\overset{R^1}{\diagup}}\overset{CF_3}{\diagup}$$

| Ex. No. | R⁴ | R³ | n | R² | R¹ | Yield (%) | Physical property | Appearance |
|---|---|---|---|---|---|---|---|---|
| 119 | 2-F-C₆H₄ | CH₃ | 0 | H | C₂H₅ | 98.2 | IR: 1685, 1485, 1150 | pale brown viscous liquid |
| 120 | 2-OCH₃-C₆H₄ | CH₃ | 0 | H | C₂H₅ | 96.7 | mp: 55.0–57.0 | colorless crystals |
| 121 | 3-CH₃O-C₆H₄ | CH₃ | 0 | H | C₂H₅ | 89.3 | mp: 46.0–48.0 | pale brown crystals |
| 122 | 3-CH₃-C₆H₄ | CH₃ | 0 | H | C₂H₅ | 75.9 | mp: 53.0–57.0 | colorless needles |
| 123 | 2,3-(CH₃)₂-C₆H₃ | CH₃ | 0 | H | C₂H₅ | 91.7 | mp: 75.0–77.0 | colorless brown crystals |
| 124 | 3-F-C₆H₄ | CH₃ | 0 | H | C₂H₅ | 90.5 | mp: 39.0–42.0 | pale yellow crystals |
| 125 | 2-C₂H₅-C₆H₄ | CH₃ | 0 | H | C₂H₅ | 84.2 | mp: 61.0–63.0 | colorless crystals |
| 126 | 4-Cl-C₆H₄ | CH₃ | 0 | H | C₂H₅ | 73.5 | mp: 89.0–90.0 | colorless plates |
| 127 | 4-CH₃-C₆H₄ | CH₃ | 0 | H | C₂H₅ | 89.6 | IR: 1675, 1482, 1145 | pale yellow viscous liquid |
| 128 | 4-F-C₆H₄ | CH₃ | 0 | H | C₂H₅ | 74.3 | IR: 1680, 1485, 1150 mp: 66.0–68.0 | pale yellow crystals |

Preparation 1

3-Trifluoromethyl-4-phenyl-5-chloroisoxazole

To 2.28 g (10.0 mmole) of 3-trifluoromethyl-4-phenyl-5-aminoisoxazole were added 20 ml of conc. HCl and 1.09 g (11. 0 mmole) of cuprous chloride and 4.2 ml of aqueous sodium nitrate (2.76 g, 40 mmole) was added dropwise to the reaction mixture, keeping the temperature at 20°-25° C. After addition, the temperature was raised to 40°-45° C. and the mixture was stirred for 1 hour. To the mixture was added 16 ml of water, extracted with methylene chloride, dried with anhydrous sodium sulfate, evaporated under reduced pressure. The residue was purified by chromatography on silica gel to give 0.5651 g of colorless liquid. This was distilled under reduced pressure to give 0.4193 g of the titled compound as colorless liquid, yield 16.9%, b.p. 80.0°-83.0° C./0.50 mmHg.

Anal. Calcd. for $C_{10}H_5NOClF_3$: C, 48.51; H, 2.04; N, 5.66; Cl, 14.32. Found C, 48.29; H, 2.23; N, 5.75; Cl, 14.90.

Preparation 2

3-Trifluoromethyl-5-chloroisoxazole

The titled compound as tan liquid was prepared according to the same procedure as described in preparation 1, b.p. 70.0° C./5.0 mmHg.

Preparation 3

2-(3-Trifluoromethyl-4-methyl-5-isoxazolyloxy)acetic acid

To 4 ml of methanol were 0.73 g (3.2 mmole) of methyl 2-(3-trifluoromethyl-4-methyl-5-isoxazolyloxy) acetate and 6 ml of 2.5% aqueous NaOH (3.6 mmole) and the resulting mixture was stirred for 3 hours. To the reaction mixture was added 100 ml of 1% aqueous HCl, extracted with diethyl ether. The diethyl ether phase was dried with anhydrous sodium sulfate and evaporated under reduced pressure to give 0.65 g of the titled compound as pale yellow crystals, yield 90.2%, m.p. 73.5°-76.0° C.

IR(CHCl$_3$, cm$^{-1}$): 1750, 1660, 1490, 1300.

In the following examples wherein parts are by weight.

Formulation Example 1

Fifty parts of the compound (I) of the present invention, 3 parts of calcium ligninsulfonate, 5 parts of sodium laurylsulfate, 2 parts of white carbon and 40 parts of clay are well mixed while being powdered to obtain a wettable powder.

Formulation Example 2

Forty parts of the compound (I) of the present invention, 5 parts of polyoxyethylenestyrylphenyl ether, 3 parts of calcium dodecylbenzenesulfonate, 30 parts of xylene and 22 parts of cyclohexanone are well mixed to obtain an emulsifiable concentrate.

Formulation Example 3

Three parts of the compound (I) of the present invention, 3 parts of polyoxyethylenealkylsulfate, 2 parts of calcium ligninsulfate, 20 parts of bentonite and 72 parts of kaolin clay are well mixed while being powdered. The mixture is then kneaded, granulated and dried to obtain granules.

Formulation Example 4

Thirty parts of the compound (I) of the present invention is mixed with 5 parts of polyoxyethylene sorbitan monooleate, 3 parts of CMC and 60 parts of water and pulverized until the particle size of the mixture becomes less than 2 microns to obtain a suspension.

It has now been found that the present compounds (I) showed a strong herbicidal activity against monocotyledonous and dicotyledonous weeds, of which typical examples in paddy fields are Gramineous weeds such as common barnyardgrass (*Echinochloa oryzicola*) broadleaf weeds such as pickerelweed (*Monochoria vaginalis*), *Vandellia anagustifolia*, toothcup (*Rotala indica*) and arrowhead (*Sagittaria pygmaea*); Cyperaceous weeds such as umbrella plant (*Cyperus difformis*), bulrush (*Scirpus juncoides SUBSP.*), slender spikerush (*Eleocharis acicularis*), waterchestnut (*Eleocharis Kuroguwai*) and perennial sedge (*Cyperus serotinus*); in upland fields are such as large crabgrass (*Digitaria adscendens*) and barnyardgrass (*Echinochloa crus-galli*). The herbicidal doses of the compounds (I) exert no or little phytotoxicity to useful plants such as rice plant, wheat, soybean and cotton, and the phytotoxicity is recoverable even if the compounds produce it. Accordingly, the present compounds (I) can be used as pre-emergence application herbicides and post-emergence application herbicides applicable to agricultural fields such as upland field, paddy field, pasture land, orchards, tea plantations, mulberry field and non-crop land as well as non-agricultural fields such as lawn, park green, woodland, man-made land, vacant land, hausing-land, factory site, riverbed, railway and roadway.

Further, the present compounds (I), too, show a stable activity by soil incorporation, which the herbicidal effects of conventional herbicides are lowered in general. Particularly, in paddy field condition, the compounds (I) produces an enhanced residual effect and herbicidal activity, and the herbicidal spectrum of the compounds (I) can be enlarged, while the phytotoxicity to rice plants is much more reduced.

In addition, as the compounds (I) are non-toxic to human, domestic animals, fowls etc. and low fish toxicity, they are safety and do not cause any residual toxicity.

The biological effect of the present compounds (I) as herbicides will be illustratively shown in the following. Examples wherein the phytotoxicity to crop plants and the herbicidal activity on weeds were evaluated visually according to a score from 0 (no damage)—5 (complete kill).

Test Example 1

The test of herbicidal activity in paddy field (1) Pre-emergence application

Paddy field soil were fed in Wagner's pots of 1/10000 are and the pots were saturated with water. Thereafter, rice seedlings (Nihonbare) in 2.5-leaf stage were transplanted. In addition, seeds of barnyardgrass, umbrella plant, pickerelweed, Vandellia and toothcup were planted therein.

On 7th day of the transplanting (two days after the sowing: pre-emergence), a designed amount of the test compound was diluted with 5 ml per pot of water and the dilution was added dropwise with pipet to the water of the pot. After the treatment, the test plants were grown for three weeks in a greenhouse, and the herbicidal activity and the phytotoxicity were examined. The results are shown in Table 3 and 4.

(2) Pre-emergence application

Paddy field soil were fed in Wagner's pots of 1/10000 are and the pots were saturated with water. Thereafter, rice seedlings (Nihonnbare) in 2.5-leaf stage were transplanted. In addition, seeds of slender spikerush, water chestnut, nutsedge, arrowhead, bog pondweed and bulrush were planted therein.

On 7th day of the transplanting (two days after the sowing: pre-emergence), a designed amount of the test compound was diluted with 5 ml per pot of water and the dilution was added dropwise with pipet to the water of the pot. After the treatment, the test plants were grown for four weeks in a greenhouse, and the herbicidal activity and the phytotoxicity were evaluated. The results are shown in Table 5.

(3) Post-emergence application

Paddy field soil were fed in Wagner's pots of 1/10000 are and the pots were saturated with water. Thereafter, rice seedlings (Nihonbare) in 2.5-leaf stage were transplanted. In addition, seeds of common barnyardgrass, umbrella plant, pickerelweed, Vandellia and toothcup were sown therein.

On 14th day of the transplantation (eight days after the sowing: post-emergence), a designed amount of the test compound was diluted with 5 ml per pot of water and the dilution was added dropwise with pipet to the surface of the pot. After the treatment, the test plants were grown for three weeks in a greenhouse, and the herbicidal activity and the phytotoxicity were evaluated. The results are shown in Tables 6 and 7.

Test example 2

The test of herbicidal activity in upland field

(1) Pre-emergence application

Upland field soil were fed in square-shaped polyvinyl pots (10×10 cm²(area)). 20 seeds of large crabgrass, barnyardgrass, pale smartweed and green amaranth, respectively, were planted in 0.5 cm soil depth in a pot and 5–10 seeds of corn, wheat, soybean, cotton, beat, rape and tomato in 1 cm depth.

Immediately thereafter, a designed amount of the test compound was diluted with 10 l per are of water and then Tween-20 (available from Nakarai Chemical Co.) corresponding to the amount of 100 ppm was added therein, and the dilution was sprayed uniformly onto the soil by means of an automatic pressure sprayer. After the treatment, the test plants were grown for four weeks in a greenhouse at 25° C., and the herbicidal activity on various weed plants and the phytotoxicity to crop plants were evaluated. The results are shown in Tables 8 and 9.

(2) Post-emergence application

Upland field soil were fed in polyvinyl pots (10×10 cm²(area)). 20 seeds of large crabgrass, barnyardgrass, pale smartweed and green amaranth, respectively, were planted in a pot and 5–10 seeds of corn, wheat, soybean, cotton, beat, rape and tomato, respectively, and they were grown in a green-house. Seven days after the planting at 2 leaf stage of large crabgrass (barnyardgrass, 2 leaf stage; pale smartweed and green amaranth, 1 leaf stage; beat, rape and tomato, cotyledon stage), a designed amount of the test compound was diluted with 10 l/are of water containing Tween −20 corresponding to the amount of 100 ppm as a spreading agent and sprayed to the foliage of the test plants. After the treatment, the test plants were grown for three weeks in a glass greenhouse at 25° C., and the herbicidal activity and the phytotoxicity were evaluated. The results are shown in Tables 10 and 11.

TABLE 3

| Comp. (Ex. No.) | Dosage (g/are) | Herbicidal activity (pre-emergence application) Weeds | | | | | Crop rice plant |
|---|---|---|---|---|---|---|---|
| | | barn-yard-grass | umbrella plant | pickerel-weed | Van-dellia | tooth-cup | |
| 1 | 20 | 5 | 5 | 5 | 4 | 3 | 4 |
| | 10 | 5 | 5 | 5 | 4 | 3 | 4 |
| | 5 | 5 | 5 | 5 | 4 | 3 | 3 |
| | 2.5 | 5 | 5 | 5 | 4 | 3 | 2 |
| 2 | 20 | 5 | 5 | 5 | 4 | 3 | 4 |
| | 10 | 5 | 5 | 4 | 4 | 3 | 3 |
| | 5 | 4 | 5 | 4 | 3 | 3 | 1 |
| | 2.5 | 4 | 5 | 4 | 3 | 2 | 0 |
| 3 | 20 | 5 | 5 | 4 | 4 | 4 | 0 |
| | 10 | 5 | 5 | 4 | 4 | 4 | 0 |
| | 5 | 5 | 5 | 4 | 4 | 4 | 0 |
| | 2.5 | 5 | 5 | 4 | 4 | 4 | 0 |
| | 1.2 | 5 | 5 | 4 | 4 | 4 | 0 |
| | 0.6 | 5 | 5 | 4 | 4 | 4 | 0 |
| | 0.3 | 4 | 5 | 4 | 4 | 2 | 0 |
| 14 | 20 | 5 | 5 | 4 | 3 | 4 | 3 |
| | 10 | 5 | 5 | 3 | 1 | 4 | 3 |
| | 5 | 5 | 3 | 1 | 0 | 2 | 1 |
| | 2.5 | 5 | 1 | 0 | 0 | 0 | 0 |
| 15 | 20 | 5 | 5 | 5 | 4 | 4 | 4 |
| | 10 | 5 | 5 | 4 | 3 | 4 | 3 |
| | 5 | 5 | 5 | 4 | 3 | 3 | 2 |
| | 2.5 | 4 | 4 | 2 | 2 | 2 | 1 |
| 17 | 20 | 5 | 5 | 4 | 4 | 5 | 1 |
| | 10 | 5 | 5 | 4 | 4 | 4 | 0 |
| | 5 | 5 | 4 | 2 | 2 | 2 | 0 |
| | 2.5 | 5 | 2 | 1 | 0 | 1 | 0 |
| 18 | 20 | 5 | 5 | 4 | 5 | 4 | 0 |
| | 10 | 4 | 5 | 3 | 4 | 3 | 0 |
| | 5 | 3 | 3 | 0 | 2 | 1 | 0 |
| | 2.5 | 3 | 1 | 0 | 0 | 0 | 0 |
| 19 | 20 | 5 | 5 | 5 | 4 | 3 | 4 |
| | 10 | 5 | 5 | 5 | 4 | 3 | 4 |
| | 5 | 5 | 5 | 4 | 4 | 3 | 4 |
| | 2.5 | 5 | 4 | 4 | 4 | 2 | 3 |
| 20 | 20 | 5 | 5 | 5 | 3 | 3 | 4 |
| | 10 | 5 | 5 | 5 | 3 | 3 | 4 |
| | 5 | 5 | 5 | 4 | 3 | 3 | 3 |
| | 2.5 | 5 | 5 | 4 | 3 | 3 | 2 |
| 21 | 20 | 5 | 5 | 5 | 4 | 4 | 3 |
| | 10 | 5 | 5 | 5 | 4 | 4 | 2 |
| | 5 | 5 | 5 | 5 | 4 | 4 | 1 |
| | 2.5 | 5 | 5 | 5 | 4 | 3 | 0 |
| 22 | 20 | 5 | 5 | 5 | 4 | 5 | 4 |
| | 10 | 5 | 5 | 5 | 4 | 4 | 2 |
| | 5 | 5 | 5 | 5 | 4 | 4 | 1 |
| | 2.5 | 5 | 5 | 5 | 3 | 4 | 0 |
| 28 | 20 | 5 | 5 | 4 | 4 | 4 | 3 |
| | 10 | 5 | 5 | 4 | 4 | 4 | 2 |
| | 5 | 5 | 5 | 4 | 4 | 4 | 1 |
| | 2.5 | 5 | 5 | 4 | 3 | 4 | 0 |
| 30 | 20 | 5 | 5 | 4 | 4 | 4 | 4 |
| | 10 | 5 | 5 | 4 | 3 | 3 | 3 |
| | 5 | 5 | 5 | 4 | 3 | 3 | 1 |
| | 2.5 | 5 | 5 | 4 | 3 | 2 | 0 |
| 32 | 20 | 5 | 5 | 5 | 4 | 4 | 3 |
| | 10 | 5 | 5 | 4 | 4 | 4 | 3 |
| | 5 | 5 | 5 | 4 | 4 | 3 | 3 |
| | 2.5 | 5 | 5 | 4 | 4 | 4 | 1 |
| 36 | 20 | 5 | 5 | 5 | 4 | 4 | 0 |
| | 10 | 5 | 5 | 5 | 4 | 4 | 0 |
| | 5 | 5 | 5 | 5 | 4 | 4 | 0 |
| | 2.5 | 5 | 5 | 4 | 4 | 4 | 0 |
| 37 | 20 | 5 | 5 | 5 | 5 | 5 | 0 |
| | 10 | 5 | 5 | 5 | 5 | 5 | 0 |
| | 5 | 5 | 5 | 4 | 4 | 5 | 0 |
| | 2.5 | 5 | 4 | 4 | 4 | 4 | 0 |

TABLE 3-continued

| Comp. (Ex. No.) | Dosage (g/are) | barnyard-grass | umbrella plant | pickerel-weed | Van-dellia | tooth-cup | Crop rice plant |
|---|---|---|---|---|---|---|---|
| 38 | 20 | 5 | 5 | 5 | 5 | 5 | 1 |
|  | 10 | 5 | 5 | 5 | 4 | 5 | 0 |
|  | 5 | 5 | 5 | 4 | 4 | 4 | 0 |
|  | 2.5 | 5 | 5 | 4 | 4 | 4 | 0 |
| 39 | 20 | 5 | 5 | 5 | 4 | 5 | 0 |
|  | 10 | 5 | 5 | 4 | 4 | 4 | 0 |
|  | 5 | 5 | 5 | 4 | 4 | 4 | 0 |
|  | 2.5 | 5 | 5 | 4 | 3 | 4 | 0 |
| 40 | 20 | 5 | 5 | 5 | 4 | 4 | 0 |
|  | 10 | 5 | 5 | 5 | 4 | 4 | 0 |
|  | 5 | 5 | 5 | 5 | 4 | 3 | 0 |
|  | 2.5 | 5 | 5 | 5 | 3 | 3 | 0 |
| 42 | 20 | 5 | 5 | 5 | 4 | 4 | 0 |
|  | 10 | 5 | 5 | 5 | 4 | 4 | 0 |
|  | 5 | 5 | 5 | 4 | 4 | 4 | 0 |
|  | 2.5 | 5 | 5 | 4 | 4 | 4 | 0 |
| 43 | 20 | 5 | 5 | 5 | 5 | 4 | 1 |
|  | 10 | 5 | 5 | 5 | 5 | 4 | 1 |
|  | 5 | 5 | 5 | 5 | 4 | 4 | 1 |
|  | 2.5 | 5 | 5 | 4 | 3 | 3 | 1 |
| 47 | 20 | 5 | 5 | 5 | 5 | 5 | 1 |
|  | 10 | 5 | 5 | 4 | 5 | 5 | 1 |
|  | 5 | 5 | 5 | 4 | 5 | 5 | 0 |
|  | 2.5 | 5 | 5 | 4 | 4 | 4 | 0 |
|  | 1.2 | 5 | 5 | 4 | 4 | 3 | 0 |
|  | 0.6 | 5 | 5 | 4 | 4 | 2 | 0 |
|  | 0.3 | 5 | 5 | 4 | 3 | 2 | 0 |
|  | 0.15 | 3 | 5 | 3 | 2 | 1 | 0 |
| 48 | 20 | 5 | 5 | 4 | 4 | 4 | 0 |
|  | 10 | 5 | 5 | 4 | 4 | 4 | 0 |
|  | 5 | 5 | 5 | 4 | 4 | 4 | 0 |
|  | 2.5 | 5 | 5 | 4 | 4 | 4 | 0 |
| 50 | 20 | 4 | 5 | 5 | 3 | 3 | 0 |
|  | 10 | 4 | 5 | 5 | 3 | 3 | 0 |
|  | 5 | 4 | 5 | 5 | 3 | 3 | 0 |
|  | 2.5 | 4 | 5 | 4 | 3 | 3 | 0 |
| 51 | 20 | 5 | 5 | 4 | 4 | 5 | 0 |
|  | 10 | 5 | 5 | 4 | 4 | 4 | 0 |
|  | 5 | 5 | 5 | 4 | 4 | 4 | 0 |
|  | 2.5 | 5 | 5 | 4 | 4 | 4 | 0 |
| 52 | 20 | 5 | 5 | 4 | 4 | 4 | 0 |
|  | 10 | 5 | 5 | 4 | 4 | 4 | 0 |
|  | 5 | 5 | 5 | 4 | 3 | 4 | 0 |
|  | 2.5 | 5 | 5 | 4 | 2 | 4 | 0 |
| 54 | 20 | 5 | 5 | 4 | 4 | 4 | 0 |
|  | 10 | 5 | 5 | 4 | 4 | 4 | 0 |
|  | 5 | 5 | 5 | 3 | 4 | 4 | 0 |
|  | 2.5 | 5 | 5 | 2 | 3 | 3 | 0 |
| 55 | 20 | 5 | 5 | 4 | 4 | 4 | 0 |
|  | 10 | 5 | 5 | 4 | 4 | 4 | 0 |
|  | 5 | 5 | 5 | 4 | 4 | 4 | 0 |
|  | 2.5 | 5 | 5 | 4 | 4 | 3 | 0 |
| 57 | 20 | 5 | 5 | 5 | 5 | 5 | 1 |
|  | 10 | 5 | 5 | 5 | 5 | 4 | 0 |
|  | 5 | 5 | 5 | 4 | 3 | 4 | 0 |
|  | 2.5 | 5 | 5 | 4 | 3 | 3 | 0 |
| 58 | 20 | 5 | 5 | 5 | 4 | 4 | 0 |
|  | 10 | 5 | 5 | 4 | 3 | 4 | 0 |
|  | 5 | 5 | 5 | 4 | 2 | 2 | 0 |
|  | 2.5 | 5 | 5 | 3 | 1 | 1 | 0 |
| 73 | 20 | 5 | 5 | 5 | 5 | 5 | 1 |
|  | 10 | 5 | 5 | 5 | 4 | 5 | 0 |
|  | 5 | 5 | 5 | 4 | 4 | 4 | 0 |
|  | 2.5 | 5 | 5 | 4 | 4 | 4 | 0 |
| 89 | 20 | 5 | 5 | 5 | 5 | 5 | 4 |
|  | 10 | 5 | 5 | 5 | 5 | 5 | 2 |
|  | 5 | 5 | 5 | 5 | 4 | 5 | 1 |
|  | 2.5 | 5 | 5 | 4 | 4 | 4 | 0 |
| 91 | 20 | 5 | 5 | 5 | 4 | 3 | 4 |
|  | 10 | 5 | 5 | 4 | 4 | 3 | 3 |
|  | 5 | 4 | 5 | 4 | 3 | 3 | 1 |
|  | 2.5 | 4 | 5 | 4 | 3 | 2 | 0 |
| 98 | 20 | 5 | 5 | 5 | 4 | 4 | 0 |
|  | 10 | 5 | 5 | 5 | 4 | 4 | 0 |
|  | 5 | 5 | 5 | 5 | 3 | 4 | 0 |
|  | 2.5 | 5 | 5 | 5 | 3 | 4 | 0 |
| 99 | 20 | 5 | 5 | 5 | 5 | 5 | 1 |
|  | 10 | 5 | 5 | 5 | 5 | 5 | 0 |
|  | 5 | 5 | 5 | 5 | 5 | 4 | 0 |
|  | 2.5 | 5 | 5 | 5 | 4 | 4 | 0 |
| 100 | 20 | 5 | 5 | 5 | 5 | 5 | 0 |
|  | 10 | 5 | 5 | 5 | 5 | 5 | 0 |
|  | 5 | 5 | 5 | 5 | 4 | 5 | 0 |
|  | 2.5 | 5 | 5 | 4 | 4 | 4 | 0 |
| Comparison (1) | 20 | 5 | 5 | 5 | 5 | 5 | 1 |
|  | 10 | 5 | 5 | 5 | 5 | 5 | 0 |
|  | 5 | 5 | 5 | 5 | 4 | 4 | 0 |
|  | 2.5 | 5 | 5 | 4 | 4 | 4 | 0 |
|  | 1.2 | 5 | 5 | 3 | 4 | 4 | 0 |
|  | 0.6 | 4-5 | 5 | 2-3 | 4 | 3-4 | 0 |
|  | 0.3 | 4-5 | 5 | 1-2 | 3-4 | 1-2 | 0 |
| Comparison (2) | 20 | 5 | 5 | 4 | 4 | 4 | 0 |
|  | 10 | 5 | 5 | 4 | 4 | 4 | 0 |
|  | 5 | 5 | 5 | 4 | 3 | 4 | 0 |
|  | 2.5 | 5 | 5 | 4 | 2 | 2 | 0 |
| Comparison (3) | 20 | 5 | 5 | 4 | 1 | 2 | 0 |
|  | 10 | 4 | 4 | 3 | 0 | 1 | 0 |
|  | 5 | 3 | 5 | 0 | 0 | 0 | 0 |
|  | 2.5 | 1 | 4 | 0 | 0 | 0 | 0 |

Note: Activity Ratings; 0 (no damage) - s (complete kill)

Comparison (1): butachlor

Comparison (2):

$$\text{Ph-N(CH}_3\text{)-C(=O)-CH}_2\text{-O-C(=N-Ph)-S}$$

(described in EP-A-37938)

Comparison (3):

$$\text{Ph-N(CH}_3\text{)-C(=O)-CH}_2\text{-O-(5-isoxazolyl, 3-phenyl)}$$

(described in EP-A-18497)

TABLE 4

| Comp. (Ex. No.) | Dosage (g/are) | Herbicidal activity (pre-emergence application) | |
|---|---|---|---|
|  |  | barnyardgrass | pickerelweed |
| 59 | 40 | 5 | 5 |
| 60 | 40 | 5 | 5 |
| 63 | 40 | 5 | 5 |
| 64 | 40 | 5 | 5 |
| 66 | 40 | 5 | 5 |
| 67 | 40 | 5 | 5 |
| 69 | 40 | 5 | 5 |
| 71 | 40 | 5 | 5 |
| 72 | 40 | 5 | 5 |
| 74 | 40 | 5 | 5 |
| 75 | 40 | 5 | 5 |
| 76 | 40 | 5 | 5 |
| 77 | 40 | 5 | 5 |
| 78 | 40 | 5 | 5 |
| 79 | 40 | 5 | 5 |

TABLE 4-continued

| Comp. (Ex. No.) | Dosage (g/are) | Herbicidal activity (pre-emergence application) | |
|---|---|---|---|
| | | barnyardgrass | pickerelweed |
| 80 | 40 | 5 | 5 |
| 81 | 40 | 5 | 5 |
| 82 | 40 | 5 | 5 |
| 83 | 40 | 5 | 5 |
| 85 | 40 | 5 | 5 |
| 87 | 40 | 5 | 2 |
| 88 | 40 | 5 | 5 |
| 90 | 40 | 5 | 5 |
| 94 | 40 | 5 | 5 |
| 95 | 40 | 5 | 5 |
| 97 | 40 | 5 | 5 |
| 101 | 40 | 5 | 5 |
| 102 | 40 | 5 | 5 |
| 103 | 40 | 5 | 5 |
| 105 | 40 | 5 | 5 |
| 106 | 40 | 5 | 5 |
| 107 | 40 | 5 | 5 |
| 109 | 40 | 5 | 5 |
| 110 | 40 | 5 | 5 |
| 112 | 40 | 5 | 5 |
| 116 | 40 | 5 | 5 |
| 117 | 40 | 5 | 5 |
| 118 | 40 | 5 | 5 |
| 119 | 40 | 5 | 5 |
| 120 | 40 | 5 | 5 |
| 123 | 40 | 5 | 5 |

TABLE 5

| Comp. (Ex. No.) | Dosage (g/are) | Herbicidal activity (pre-emergence application) | | | | | | Crop rice plant |
|---|---|---|---|---|---|---|---|---|
| | | slender spikerush | water chestnut | perennial sedge | arrowhead | bog pondweed | hardstem bulrush | |
| 3 | 20 | 4 | 4 | 4 | 2 | 4 | 5 | 1 |
| | 10 | 4 | 4 | 4 | 2 | 4 | 5 | 0 |
| | 5 | 3 | 4 | 4 | 1 | 4 | 5 | 0 |
| | 2.5 | 3 | 3 | 3 | 0 | 3 | 5 | 0 |
| 47 | 20 | 5 | 4 | 4–5 | 2 | 4 | 5 | 2 |
| | 10 | 4 | 3 | 3–4 | 2 | 4 | 5 | 1 |
| | 5 | 4 | 3 | 2–3 | 0 | 4 | 5 | 1 |
| | 2.5 | 4 | 2 | 2 | 0 | 4 | 5 | 0 |
| 48 | 20 | 3 | 3 | 3 | 1 | 4 | 5 | 0 |
| | 10 | 3 | 3 | 3 | 1 | 4 | 5 | 0 |
| | 5 | 3 | 2 | 3 | 1 | 2 | 4 | 0 |
| | 2.5 | 3 | 1 | 2 | 0 | 0 | 4 | 0 |
| Comparison (1) | 20 | 5 | 4 | 4 | 4 | 1 | 5 | 1 |
| | 10 | 5 | 4 | 4 | 3 | 1 | 5 | 1 |
| | 5 | 4 | 3 | 4 | 1 | 0 | 5 | 0 |
| | 2.5 | 4 | 1 | 3 | 0 | 0 | 5 | 0 |

Comparison (1) is as described above.

TABLE 6

| Comp. (Ex. No.) | Dosage (g/are) | Herbicidal activity (post-emergence application) | | | | | Crop rice plant |
|---|---|---|---|---|---|---|---|
| | | barnyardgrass | umbrella plant | pickerelweed | Vandellia | toothcup | |
| 3 | 20 | 4 | 4 | 4 | 1 | 2 | 0 |
| | 10 | 4 | 4 | 4 | 1 | 2 | 0 |
| | 5 | 4 | 4 | 3 | 1 | 2 | 0 |
| | 2.5 | 4 | 4 | 3 | 1 | 2 | 0 |
| | 1.2 | 4 | 3 | 3 | 1 | 2 | 0 |
| | 0.6 | 4 | 2 | 3 | 1 | 2 | 0 |
| | 0.3 | 3 | 2 | 2 | 1 | 2 | 0 |
| 18 | 20 | 4 | 3 | 3 | 1 | 0 | 0 |
| | 10 | 4 | 3 | 1 | 0 | 0 | 0 |
| | 5 | 2 | 1 | 0 | 0 | 0 | 0 |
| | 2.5 | 1 | 0 | 0 | 0 | 0 | 0 |
| 22 | 20 | 4 | 4 | 4 | 3 | 4 | 1 |
| | 10 | 4 | 4 | 4 | 3 | 3 | 1 |
| | 5 | 4 | 4 | 4 | 2 | 3 | 0 |
| | 2.5 | 4 | 4 | 4 | 2 | 3 | 0 |
| 28 | 20 | 5 | 5 | 4 | 2 | 2 | 2 |
| | 10 | 5 | 4 | 4 | 2 | 2 | 1 |
| | 5 | 5 | 4 | 4 | 1 | 1 | 0 |
| | 2.5 | 4 | 3 | 2 | 1 | 1 | 0 |
| 36 | 20 | 4 | 5 | 3 | 2 | 3 | 1 |
| | 10 | 4 | 4 | 3 | 2 | 3 | 0 |
| | 5 | 4 | 4 | 3 | 1 | 3 | 0 |
| | 2.5 | 4 | 3 | 3 | 1 | 3 | 0 |
| 37 | 20 | 4 | 4 | 4 | 2 | 3 | 1 |
| | 10 | 4 | 4 | 4 | 1 | 3 | 0 |
| | 5 | 4 | 4 | 3 | 1 | 3 | 0 |
| | 2.5 | 3 | 3 | 3 | 1 | 2 | 0 |
| 38 | 20 | 4 | 4 | 4 | 2 | 3 | 2 |
| | 10 | 4 | 4 | 4 | 2 | 2 | 1 |
| | 5 | 3 | 4 | 3 | 2 | 2 | 0 |
| | 2.5 | 3 | 4 | 3 | 2 | 1 | 0 |
| 39 | 20 | 4 | 4 | 3 | 3 | 3 | 0 |
| | 10 | 4 | 3 | 3 | 2 | 2 | 0 |
| | 5 | 3 | 3 | 2 | 1 | 1 | 0 |
| | 2.5 | 2 | 3 | 2 | 1 | 1 | 0 |
| 40 | 20 | 4 | 4 | 4 | 1 | 3 | 0 |
| | 10 | 4 | 4 | 3 | 1 | 3 | 0 |
| | 5 | 4 | 4 | 3 | 1 | 2 | 0 |
| | 2.5 | 4 | 4 | 3 | 1 | 2 | 0 |
| 42 | 20 | 4 | 5 | 4 | 2 | 3 | 1 |
| | 10 | 4 | 5 | 3 | 2 | 3 | 0 |
| | 5 | 4 | 5 | 3 | 1 | 2 | 0 |
| | 2.5 | 4 | 4 | 3 | 1 | 2 | 0 |
| 43 | 20 | 4 | 4 | 4 | 1 | 2 | 0 |
| | 10 | 4 | 4 | 3 | 1 | 2 | 0 |
| | 5 | 4 | 4 | 2 | 1 | 1 | 0 |
| | 2.5 | 3 | 3 | 2 | 1 | 1 | 0 |
| 47 | 20 | 5 | 5 | 4 | 5 | 3 | 0 |
| | 10 | 5 | 5 | 4 | 5 | 3 | 0 |
| | 5 | 4 | 5 | 3 | 5 | 3 | 0 |
| | 2.5 | 4 | 5 | 3 | 4 | 3 | 0 |
| 48 | 20 | 4 | 4 | 4 | 1 | 2 | 0 |
| | 10 | 4 | 4 | 4 | 1 | 2 | 0 |
| | 5 | 4 | 4 | 3 | 1 | 2 | 0 |
| | 2.5 | 4 | 3 | 2 | 0 | 2 | 0 |
| 52 | 20 | 4 | 3 | 3 | 1 | 2 | 0 |
| | 10 | 4 | 3 | 2 | 1 | 2 | 0 |
| | 5 | 3 | 3 | 2 | 0 | 1 | 0 |
| | 2.5 | 2 | 3 | 2 | 0 | 1 | 0 |
| 57 | 20 | 4 | 4 | 4 | 2 | 3 | 3 |
| | 10 | 4 | 4 | 4 | 1 | 1 | 1 |
| | 5 | 4 | 4 | 3 | 1 | 1 | 0 |
| | 2.5 | 4 | 4 | 2 | 0 | 0 | 0 |
| 58 | 20 | 4 | 4 | 4 | 4 | 3 | 0 |
| | 10 | 4 | 4 | 3 | 3 | 3 | 0 |
| | 5 | 4 | 4 | 2 | 3 | 3 | 0 |
| | 2.5 | 4 | 4 | 1 | 1 | 1 | 0 |

TABLE 6-continued

| | | Herbicidal activity (post-emergence application) | | | | | |
|---|---|---|---|---|---|---|---|
| | | Weeds | | | | | |
| Comp. (Ex. No.) | Dosage (g/are) | barn-yard-grass | umbrella plant | pickerel-weed | Van-dellia | tooth-cup | Crop rice plant |
| 73 | 20 | 4 | 5 | 4 | 4 | 4 | 1 |
| | 10 | 4 | 5 | 4 | 4 | 4 | 0 |
| | 5 | 4 | 5 | 4 | 3 | 4 | 0 |
| | 2.5 | 4 | 4 | 3 | 3 | 3 | 0 |
| 89 | 20 | 5 | 5 | 4 | 4 | 4 | 4 |
| | 10 | 5 | 5 | 4 | 4 | 4 | 3 |
| | 5 | 4 | 4 | 4 | 3 | 4 | 1 |
| | 2.5 | 4 | 4 | 4 | 3 | 4 | 1 |
| 98 | 20 | 4 | 4 | 4 | 3 | 3 | 0 |
| | 10 | 4 | 4 | 4 | 3 | 3 | 0 |
| | 5 | 4 | 4 | 4 | 3 | 3 | 0 |
| | 2.5 | 4 | 3 | 3 | 3 | 2 | 0 |
| 99 | 20 | 4–5 | 5 | 4 | 3 | 4 | 0 |
| | 10 | 4–5 | 5 | 3 | 3 | 3 | 0 |
| | 5 | 4 | 5 | 3 | 3 | 3 | 0 |
| | 2.5 | 4 | 5 | 1 | 2 | 2 | 0 |
| 100 | 20 | 4–5 | 5 | 4 | 3 | 4 | 0 |
| | 10 | 4–5 | 5 | 3 | 3 | 4 | 0 |
| | 5 | 4–5 | 5 | 3 | 3 | 3 | 0 |
| | 2.5 | 4–5 | 4 | 1 | 2 | 3 | 0 |
| Comparison (1) | 20 | 5 | 4 | 4 | 1 | 3 | 1 |
| | 10 | 5 | 4 | 3 | 0 | 3 | 0 |
| | 5 | 5 | 4 | 3 | 0 | 3 | 0 |
| | 2.5 | 5 | 3 | 2 | 0 | 3 | 0 |
| Comparison (2) | 20 | 5 | 5 | 4 | 4 | 4 | 2 |
| | 10 | 5 | 5 | 4 | 4 | 4 | 1 |
| | 5 | 5 | 4 | 4 | 4 | 4 | 0 |
| | 2.5 | 4 | 4 | 4 | 3 | 3 | 0 |
| | 1.2 | 4 | 3 | 1 | 0 | 2 | 0 |
| | 0.6 | 4 | 2 | 0 | 0 | 0 | 0 |
| | 0.3 | 2 | 2 | 0 | 0 | 0 | 0 |
| Comparison (3) | 20 | 3 | 4 | 1 | 0 | 1 | 0 |
| | 10 | 3 | 4 | 0 | 0 | 0 | 0 |
| | 5 | 2 | 4 | 0 | 0 | 0 | 0 |
| | 2.5 | 0 | 3 | 0 | 0 | 0 | 0 |

Comparisons (1) to (3) are as described above.

TABLE 7

| Comp. (Ex. No.) | Dosage (g/are) | Herbicidal activity barnyardgrass | (post-emergence application) pickerelweed |
|---|---|---|---|
| 59 | 40 | 5 | 5 |
| 60 | 40 | 5 | 5 |
| 66 | 40 | 5 | 5 |
| 67 | 40 | 5 | 5 |
| 69 | 40 | 4 | 3 |
| 71 | 40 | 5 | 5 |
| 72 | 40 | 5 | 5 |
| 74 | 40 | 5 | 4 |
| 75 | 40 | 5 | 5 |
| 76 | 40 | 5 | 5 |
| 77 | 40 | 5 | 5 |
| 78 | 40 | 5 | 5 |
| 79 | 40 | 5 | 5 |
| 80 | 40 | 5 | 5 |
| 81 | 40 | 5 | 5 |
| 82 | 40 | 5 | 5 |
| 83 | 40 | 5 | 4 |
| 85 | 40 | 4 | 4 |
| 87 | 40 | 3 | 2 |
| 88 | 40 | 4 | 3 |
| 91 | 40 | 5 | 4 |
| 94 | 40 | 5 | 4 |
| 95 | 40 | 5 | 3 |
| 97 | 40 | 5 | 3 |
| 101 | 40 | 4 | 1 |
| 102 | 40 | 5 | 5 |
| 103 | 40 | 4 | 5 |
| 105 | 40 | 5 | 5 |
| 106 | 40 | 5 | 5 |
| 107 | 40 | 5 | 5 |
| 109 | 40 | 4 | 5 |
| 110 | 40 | 5 | 5 |
| 112 | 40 | 4 | 5 |
| 116 | 40 | 5 | 5 |
| 117 | 40 | 5 | 5 |
| 118 | 40 | 5 | 5 |
| 119 | 40 | 5 | 5 |
| 120 | 40 | 5 | 5 |
| 123 | 40 | 5 | 5 |

TABLE 8

| | | Herbicidal activity (pre-emergence application) | | | | | | | | | | |
|---|---|---|---|---|---|---|---|---|---|---|---|---|
| | | Weeds | | | | Crops | | | | | | |
| Comp. (Ex. No.) | Dosage (g/are) | large crabgrass | barnyard-grass | pale smartweed | green amaranth | corn | wheat | soy-bean | cotton | beet | rape | tomato |
| 1 | 20 | 5 | 5 | 4 | 5 | 3 | 0 | 1 | 0 | 3 | 5 | 5 |
| | 10 | 5 | 5 | 2 | 5 | 3 | 0 | 0 | 0 | 2 | 3 | 3 |
| | 5 | 5 | 5 | 2 | 3 | 0 | 0 | 0 | 0 | 0 | 2 | 1 |
| | 2.5 | 5 | 5 | 0 | 2 | 0 | 0 | 0 | 0 | 0 | 0 | 0 |
| 2 | 20 | 5 | 5 | 3 | 5 | 2 | 0 | 1 | 0 | 2 | 2 | 2 |
| | 10 | 4 | 5 | 2 | 4 | 1 | 0 | 0 | 0 | 2 | 2 | 1 |
| | 5 | 4 | 4 | 1 | 2 | 0 | 0 | 0 | 0 | 1 | 0 | 1 |
| | 2.5 | 2 | 2 | 0 | 0 | 0 | 0 | 0 | 0 | 0 | 0 | 0 |
| 3 | 20 | 5 | 5 | 3 | 4 | 0 | 0 | 0 | 0 | 0 | 0 | 0 |
| | 10 | 5 | 5 | 2 | 4 | 0 | 0 | 0 | 0 | 0 | 0 | 0 |
| | 5 | 5 | 4 | 2 | 4 | 0 | 0 | 0 | 0 | 0 | 0 | 0 |
| | 2.5 | 4 | 2 | 2 | 4 | 0 | 0 | 0 | 0 | 0 | 0 | 0 |
| 14 | 20 | 5 | 5 | 1 | 2 | 0 | 2 | 0 | 0 | 0 | 2 | 2 |
| | 10 | 5 | 3 | 0 | 0 | 0 | 0 | 0 | 0 | 0 | 2 | 1 |
| | 5 | 2 | 0 | 0 | 0 | 0 | 0 | 0 | 0 | 0 | 0 | 0 |
| | 2.5 | 2 | 0 | 0 | 0 | 0 | 0 | 0 | 0 | 0 | 0 | 0 |
| 15 | 20 | 5 | 5 | 0 | 3 | 1 | 0 | 0 | 0 | 0 | 0 | 1 |
| | 10 | 5 | 4 | 0 | 1 | 0 | 0 | 0 | 0 | 0 | 0 | 0 |
| | 5 | 2 | 1 | 0 | 0 | 0 | 0 | 0 | 0 | 0 | 0 | 0 |
| | 2.5 | 2 | 0 | 0 | 0 | 0 | 0 | 0 | 0 | 0 | 0 | 0 |
| 17 | 20 | 5 | 5 | 0 | 3 | 3 | 2 | 0 | 0 | 2 | 1 | 1 |
| | 10 | 5 | 5 | 0 | 2 | 2 | 1 | 0 | 0 | 1 | 0 | 1 |
| | 5 | 3 | 2 | 0 | 0 | 1 | 0 | 0 | 0 | 0 | 0 | 0 |
| | 2.5 | 2 | 0 | 0 | 0 | 0 | 0 | 0 | 0 | 0 | 0 | 0 |
| 19 | 20 | 5 | 5 | 4 | 5 | 3 | 3 | 2 | 0 | 2 | 2 | 2 |
| | 10 | 5 | 5 | 2 | 5 | 2 | 2 | 1 | 0 | 1 | 1 | 1 |
| | 5 | 5 | 5 | 4 | 2 | 0 | 0 | 1 | 0 | 0 | 0 | 0 |
| | 2.5 | 5 | 3 | 3 | 2 | 0 | 0 | 0 | 0 | 0 | 0 | 0 |
| 20 | 20 | 5 | 5 | 4 | 5 | 1 | 1 | 0 | 2 | 2 | 2 | 4 |
| | 10 | 5 | 5 | 2 | 5 | 0 | 0 | 0 | 1 | 0 | 0 | 2 |
| | 5 | 5 | 5 | 4 | 0 | 4 | 0 | 0 | 0 | 0 | 0 | 0 |

TABLE 8-continued

|  |  | Herbicidal activity (pre-emergence application) | | | | | | | | | | |
|---|---|---|---|---|---|---|---|---|---|---|---|---|
|  |  | Weeds | | | | Crops | | | | | | |
| Comp. (Ex. No.) | Dosage (g/are) | large crabgrass | barnyard-grass | pale smartweed | green amaranth | corn | wheat | soy-bean | cotton | beet | rape | tomato |
|  | 2.5 | 3 | 4 | 0 | 2 | 0 | 0 | 0 | 0 | 0 | 0 | 0 |
|  | 20 | 5 | 5 | 2 | 3 | 1 | 1 | 0 | 0 | 0 | 1 | 2 |
| 21 | 10 | 4 | 5 | 2 | 2 | 0 | 1 | 0 | 0 | 0 | 0 | 2 |
|  | 5 | 4 | 5 | 2 | 2 | 0 | 0 | 0 | 0 | 0 | 0 | 0 |
|  | 2.5 | 4 | 3 | 1 | 2 | 0 | 0 | 0 | 0 | 0 | 0 | 0 |
|  | 20 | 5 | 5 | 3 | 3 | 2 | 1 | 2 | 1 | 1 | 2 | 3 |
| 27 | 10 | 5 | 5 | 3 | 3 | 0 | 0 | 2 | 0 | 1 | 1 | 2 |
|  | 5 | 5 | 4 | 2 | 2 | 0 | 0 | 0 | 0 | 0 | 0 | 1 |
|  | 2.5 | 4 | 4 | 1 | 2 | 0 | 0 | 0 | 0 | 0 | 0 | 1 |
|  | 20 | 5 | 5 | 5 | 5 | 0 | 1 | 1 | 2 | 2 | 3 | 3 |
| 28 | 10 | 5 | 5 | 4 | 4 | 0 | 1 | 1 | 0 | 2 | 2 | 2 |
|  | 5 | 5 | 5 | 3 | 4 | 0 | 0 | 0 | 0 | 0 | 0 | 0 |
|  | 2.5 | 4 | 4 | 2 | 3 | 0 | 0 | 0 | 0 | 0 | 0 | 0 |
|  | 20 | 5 | 5 | 5 | 5 | 4 | 2 | 2 | 0 | 2 | 2 | 3 |
| 30 | 10 | 5 | 5 | 3 | 5 | 2 | 2 | 2 | 0 | 2 | 2 | 0 |
|  | 5 | 5 | 5 | 2 | 5 | 1 | 0 | 0 | 0 | 0 | 2 | 0 |
|  | 2.5 | 5 | 5 | 2 | 0 | 0 | 0 | 0 | 0 | 0 | 2 | 0 |
|  | 20 | 5 | 5 | 4 | 5 | 3 | 2 | 0 | 1 | 4 | 3 | 5 |
| 32 | 10 | 5 | 5 | 4 | 5 | 0 | 0 | 0 | 1 | 3 | 2 | 4 |
|  | 5 | 5 | 5 | 3 | 4 | 0 | 0 | 0 | 0 | 2 | 2 | 3 |
|  | 2.5 | 5 | 5 | 2 | 4 | 0 | 0 | 0 | 0 | 0 | 0 | 2 |
|  | 20 | 5 | 5 | 0 | 3 | 1 | 0 | 0 | 2 | 4 | 2 | 5 |
| 37 | 10 | 5 | 5 | 0 | 3 | 1 | 0 | 0 | 2 | 3 | 1 | 2 |
|  | 5 | 4 | 4 | 0 | 0 | 1 | 0 | 0 | 2 | 3 | 0 | 2 |
|  | 2.5 | 4 | 3 | 0 | 0 | 0 | 0 | 0 | 0 | 0 | 0 | 2 |
|  | 20 | 5 | 5 | 3 | 4 | 1 | 2 | 2 | 0 | 2 | 2 | 2 |
| 38 | 10 | 5 | 5 | 2 | 2 | 1 | 2 | 0 | 0 | 2 | 2 | 2 |
|  | 5 | 5 | 4 | 1 | 2 | 0 | 1 | 0 | 0 | 2 | 1 | 2 |
|  | 2.5 | 4 | 4 | 0 | 2 | 0 | 0 | 0 | 0 | 2 | 1 | 2 |
|  | 20 | 5 | 5 | 2 | 5 | 2 | 1 | 0 | 0 | 2 | 2 | 0 |
| 42 | 10 | 5 | 4 | 2 | 5 | 1 | 1 | 0 | 0 | 1 | 2 | 0 |
|  | 5 | 5 | 3 | 0 | 4 | 0 | 0 | 0 | 0 | 0 | 0 | 0 |
|  | 2.5 | 4 | 3 | 0 | 2 | 0 | 0 | 0 | 0 | 0 | 0 | 0 |
|  | 20 | 5 | 5 | 3 | 3 | 1 | 2 | 1 | 0 | 2 | 2 | 1 |
| 58 | 10 | 4 | 4 | 3 | 2 | 1 | 1 | 0 | 0 | 2 | 2 | 0 |
|  | 5 | 4 | 3 | 2 | 1 | 0 | 0 | 0 | 0 | 0 | 0 | 0 |
|  | 2.5 | 3 | 2 | 2 | 1 | 0 | 0 | 0 | 0 | 0 | 0 | 0 |
|  | 20 | 5 | 5 | 4 | 5 | 2 | 2 | 0 | 0 | 2 | 1 | 3 |
| 59 | 10 | 5 | 5 | 3 | 5 | 2 | 1 | 0 | 0 | 2 | 0 | 0 |
|  | 5 | 5 | 5 | 1 | 4 | 0 | 0 | 0 | 0 | 0 | 0 | 0 |
|  | 2.5 | 4 | 3 | 0 | 4 | 0 | 0 | 0 | 0 | 0 | 0 | 0 |
|  | 20 | 5 | 5 | 5 | 5 | 3 | 3 | 2 | 0 | 3 | 4 | 4 |
| 62 | 10 | 5 | 5 | 4 | 5 | 2 | 1 | 2 | 0 | 3 | 3 | 4 |
|  | 5 | 5 | 5 | 3 | 5 | 2 | 0 | 0 | 0 | 2 | 2 | 3 |
|  | 2.5 | 5 | 5 | 2 | 3 | 2 | 0 | 0 | 0 | 1 | 1 | 2 |
|  | 20 | 5 | 5 | 5 | 5 | 3 | 3 | 4 | 2 | 5 | 4 | 5 |
| 68 | 10 | 5 | 5 | 5 | 5 | 3 | 2 | 2 | 0 | 4 | 4 | 4 |
|  | 5 | 5 | 5 | 4 | 5 | 2 | 2 | 1 | 0 | 3 | 3 | 3 |
|  | 2.5 | 5 | 5 | 3 | 5 | 0 | 1 | 1 | 0 | 2 | 3 | 2 |
|  | 20 | 5 | 5 | 4 | 5 | 4 | 2 | 2 | 2 | 3 | 4 | 5 |
| 70 | 10 | 5 | 5 | 4 | 5 | 3 | 2 | 0 | 2 | 3 | 3 | 5 |
|  | 5 | 5 | 5 | 3 | 5 | 2 | 1 | 0 | 0 | 3 | 2 | 4 |
|  | 2.5 | 5 | 5 | 2 | 5 | 1 | 0 | 0 | 0 | 3 | 1 | 3 |
|  | 20 | 5 | 5 | 2 | 3 | 2 | 2 | 0 | 0 | 0 | 2 | 2 |
| 74 | 10 | 5 | 5 | 0 | 3 | 1 | 1 | 0 | 0 | 0 | 0 | 2 |
|  | 5 | 5 | 4 | 0 | 3 | 0 | 0 | 0 | 0 | 0 | 0 | 0 |
|  | 2.5 | 4 | 4 | 0 | 3 | 0 | 0 | 0 | 0 | 0 | 0 | 0 |
|  | 20 | 5 | 5 | 2 | 2 | 2 | 2 | 0 | 0 | 0 | 2 | 2 |
| 83 | 10 | 5 | 5 | 0 | 0 | 0 | 0 | 0 | 0 | 0 | 1 | 2 |
|  | 5 | 4 | 3 | 0 | 0 | 0 | 0 | 0 | 0 | 0 | 0 | 0 |
|  | 2.5 | 4 | 3 | 0 | 0 | 0 | 0 | 0 | 0 | 0 | 0 | 0 |
|  | 20 | 5 | 5 | 3 | 5 | 2 | 0 | 1 | 0 | 2 | 2 | 2 |
| 91 | 10 | 5 | 4 | 2 | 4 | 1 | 0 | 0 | 0 | 2 | 2 | 1 |
|  | 5 | 4 | 4 | 1 | 2 | 0 | 0 | 0 | 0 | 1 | 0 | 1 |
|  | 2.5 | 2 | 2 | 0 | 0 | 0 | 0 | 0 | 0 | 0 | 0 | 0 |
|  | 20 | 5 | 5 | 4 | 5 | 4 | 3 | 2 | 2 | 3 | 4 | 5 |
| 92 | 10 | 5 | 5 | 3 | 5 | 3 | 2 | 1 | 1 | 3 | 3 | 3 |
|  | 5 | 5 | 5 | 3 | 4 | 2 | 2 | 1 | 0 | 3 | 3 | 3 |
|  | 2.5 | 4 | 5 | 3 | 4 | 1 | 2 | 0 | 0 | 2 | 2 | 3 |
|  | 20 | 5 | 5 | 4 | 5 | 3 | 3 | 3 | 2 | 3 | 4 | 3 |
| 93 | 10 | 5 | 5 | 4 | 5 | 3 | 2 | 2 | 0 | 3 | 4 | 3 |
|  | 5 | 5 | 5 | 3 | 5 | 2 | 1 | 1 | 0 | 2 | 2 | 3 |
|  | 2.5 | 5 | 5 | 2 | 5 | 0 | 0 | 1 | 0 | 2 | 2 | 3 |
|  | 20 | 5 | 5 | 3 | 5 | 2 | 2 | 2 | 0 | 2 | 3 | 4 |
| 94 | 10 | 5 | 5 | 2 | 4 | 1 | 0 | 0 | 0 | 0 | 3 | 2 |
|  | 5 | 4 | 5 | 1 | 4 | 0 | 0 | 0 | 0 | 0 | 2 | 2 |

TABLE 8-continued

| | | Herbicidal activity (pre-emergence application) | | | | | | | | | | |
|---|---|---|---|---|---|---|---|---|---|---|---|---|
| | | Weeds | | | | Crops | | | | | | |
| Comp. (Ex. No.) | Dosage (g/are) | large crabgrass | barnyard-grass | pale smartweed | green amaranth | corn | wheat | soy-bean | cotton | beet | rape | tomato |
| | 2.5 | 4 | 4 | 0 | 3 | 0 | 0 | 0 | 0 | 0 | 2 | 0 |

TABLE 9

| | | Herbicidal activity (pre-emergence application) | | | |
|---|---|---|---|---|---|
| | | Weeds | | | |
| Comp. (Ex. No.) | Dosage (g/are) | large crabgrass | barnyardgrass | pale smartweed | green amaranth |
| 5 | 40 | 5 | 5 | 5 | 5 |
| 25 | 40 | 5 | 5 | 5 | 5 |
| 57 | 40 | 5 | 5 | 5 | 5 |
| 63 | 40 | 5 | 5 | 3 | 3 |
| 64 | 40 | 5 | 5 | 2 | 1 |
| 67 | 40 | 5 | 5 | 5 | 5 |
| 69 | 40 | 5 | 5 | 4 | 5 |
| 71 | 40 | 5 | 5 | 4 | 5 |
| 72 | 40 | 5 | 5 | 4 | 5 |
| 75 | 40 | 5 | 5 | 4 | 5 |
| 76 | 40 | 5 | 5 | 5 | 5 |
| 77 | 40 | 5 | 5 | 4 | 5 |
| 78 | 40 | 5 | 5 | 4 | 3 |
| 79 | 40 | 5 | 5 | 3 | 5 |
| 80 | 40 | 5 | 5 | 4 | 5 |
| 81 | 40 | 5 | 4 | 3 | 4 |
| 82 | 40 | 5 | 5 | 4 | 5 |
| 84 | 40 | 5 | 5 | 4 | 5 |
| 85 | 40 | 5 | 5 | 4 | 3 |
| 88 | 40 | 5 | 5 | 4 | 3 |
| 89 | 40 | 5 | 5 | 5 | 5 |
| 97 | 40 | 4 | 3 | 1 | 2 |
| 102 | 40 | 5 | 5 | 0 | 0 |
| 105 | 40 | 5 | 5 | 2 | 3 |
| 106 | 40 | 5 | 5 | 0 | 0 |
| 107 | 40 | 5 | 5 | 1 | 1 |
| 109 | 40 | 5 | 4 | 0 | 0 |
| 110 | 40 | 5 | 5 | 1 | 4 |
| 118 | 40 | 5 | 4 | 4 | 5 |
| 119 | 40 | 5 | 5 | 5 | 5 |
| 120 | 40 | 5 | 5 | 4 | 5 |
| 123 | 40 | 5 | 5 | 4 | 5 |

TABLE 10

| | | Herbicidal activity (post-emergence application) | | | | | | | | | | |
|---|---|---|---|---|---|---|---|---|---|---|---|---|
| | | Weeds | | | | Crops | | | | | | |
| Comp. (Ex. No.) | Dosage (g/are) | large crabgrass | barnyard-grass | pale smartweed | green amaranth | corn | wheat | soy-bean | cotton | beet | rape | tomato |
| | 20 | 4 | 4 | 4 | 3 | 2 | 1 | 3 | 2 | 2 | 3 | 4 |
| 28 | 10 | 4 | 4 | 3 | 2 | 2 | 1 | 3 | 2 | 2 | 3 | 3 |
| | 5 | 3 | 4 | 2 | 2 | 1 | 0 | 2 | 2 | 2 | 3 | 3 |
| | 2.5 | 2 | 2 | 2 | 2 | 0 | 0 | 2 | 2 | 2 | 2 | 2 |
| | 20 | 4 | 4 | 3 | 4 | 2 | 0 | 3 | 3 | 3 | 3 | 4 |
| 32 | 10 | 4 | 4 | 3 | 4 | 0 | 0 | 3 | 3 | 3 | 3 | 3 |
| | 5 | 4 | 4 | 2 | 2 | 0 | 0 | 2 | 2 | 3 | 3 | 3 |
| | 2.5 | 4 | 4 | 2 | 2 | 0 | 0 | 2 | 2 | 3 | 3 | 3 |

TABLE 11

| | | Herbicidal activity (post-emergence application) | | | |
|---|---|---|---|---|---|
| | | Weeds | | | |
| Comp. (Ex. No.) | Dosage (g/are) | large crabgrass | barnyard-grass | pale smartweed | green amaranth |
| 5 | 40 | 4 | 4 | 5 | 3 |
| 25 | 40 | 4 | 4 | 4 | 4 |
| 57 | 40 | 4 | 4 | 4 | 3 |
| 63 | 40 | 4 | 4 | 4 | 3 |
| 64 | 40 | 4 | 4 | 3 | 2 |
| 67 | 40 | 4 | 4 | 5 | 5 |
| 69 | 40 | 4 | 4 | 4 | 4 |
| 71 | 40 | 4 | 4 | 4 | 3 |
| 72 | 40 | 4 | 4 | 4 | 4 |
| 75 | 40 | 4 | 4 | 3 | 3 |
| 76 | 40 | 4 | 4 | 4 | 4 |
| 77 | 40 | 4 | 4 | 4 | 4 |
| 78 | 40 | 4 | 4 | 3 | 3 |
| 79 | 40 | 4 | 4 | 4 | 3 |
| 80 | 40 | 4 | 4 | 3 | 4 |
| 81 | 40 | 4 | 4 | 3 | 3 |
| 82 | 40 | 4 | 4 | 4 | 3 |
| 84 | 40 | 4 | 4 | 3 | 3 |
| 85 | 40 | 4 | 4 | 3 | 2 |
| 88 | 40 | 3 | 4 | 2 | 2 |
| 89 | 40 | 4 | 4 | 4 | 2 |
| 97 | 40 | 4 | 3 | 5 | 5 |
| 102 | 40 | 4 | 4 | 3 | 2 |
| 105 | 40 | 4 | 3 | 3 | 3 |
| 106 | 40 | 3 | 4 | 4 | 3 |
| 107 | 40 | 4 | 4 | 4 | 4 |
| 109 | 40 | 3 | 2 | 2 | 2 |
| 110 | 40 | 4 | 4 | 3 | 3 |
| 118 | 40 | 4 | 4 | 4 | 4 |
| 119 | 40 | 4 | 4 | 4 | 4 |
| 120 | 40 | 4 | 4 | 4 | 4 |
| 123 | 40 | 4 | 4 | 4 | 4 |

What is claimed is:

1. A compound of the formula:

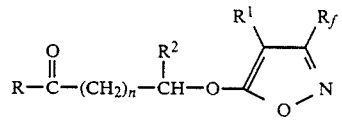

in which R is OH, $C_1$-$C_3$ alkoxy or $R^3$-N-$R^4$; $R_f$ is $C_1$-$C_6$ perfluoroalkyl; $R^1$ is hydrogen, $C_1$-$C_6$ alkyl, phenyl or phenyl substituted by chloro, fluoro, methyl, methoxy, or methylenedioxy; $R^2$ is hydrogen or $C_1$-$C_3$ alkyl; n is an integer of 0 to 2; $R^3$ is hydrogen, or $C_1$-$C_3$ alkyl; $R^4$ is $C_1$-$C_6$ alkyl, benzyl, α-methylbenzyl, α,α-dimethylbenzyl, phenylethyl, phenylpropyl, phenyl or phenyl substituted with one or two substituents selected from the group consisting of halogen, $C_1$-$C_4$ alkyl, methoxy, methylthio, methylcarbonyl, trifluoromethyl, nitro and phenyl; or $R^3$ and $R^4$ together with the nitrogen atom to which they are attached form 2-methylpiperidino 2-ethylpiperidino, morpholino or pyrrolidino; or a an agriculturally acceptable salt thereof.

2. A compound of the formula:

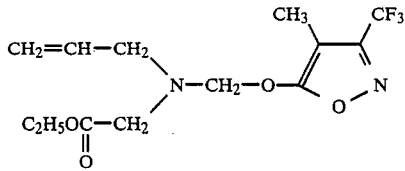

3. A herbicidal composition which comprises as an active ingredient, a herbicidally effective amount of a compound of the formula:

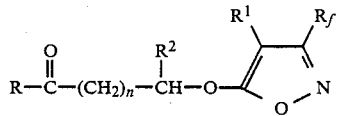

in which R is OH, $C_1$-$C_3$ alkoxy or $R^3$-N-$R^4$; $R_f$ is $C_1$-$C_3$ perfluoroalkyl; $R^1$ is hydrogen, $C_1$-$C_6$ alkyl, phenyl or phenyl substituted by chloro, fluoro, methyl, methoxy, or methylenedioxy; $R^2$ is hydrogen or $C_1$-$C_3$ alkyl; n is an integer of 0 to 2; $R^3$ is hydrogen, or $C_1$-$C_3$ alkyl; $R^4$ is $C_1$-$C_6$ alkyl, benzyl, α-methylbenzyl, α,α-dimethylbenzyl, phenylethyl, phenylpropyl, phenyl or phenyl substituted with one or two substituents selected from the group consisting of halogen, $C_1$-$C_4$ alkyl, methoxy, methylthio, methylcarbonyl, trifluoromethyl, nitro and phenyl; or $R^3$ and $R^4$ together with the nitrogen atom to which they are attached form 2-methylpiperidino, 2-ethylpiperidino, morpholino or pyrrolidino; or a an agriculturally acceptable salt thereof.

* * * * *